(12) United States Patent
Cheng et al.

(10) Patent No.: US 10,183,059 B2
(45) Date of Patent: Jan. 22, 2019

(54) METHOD FOR TREATING MICROBIAL INFECTION

(71) Applicant: GENERAL BIOLOGICALS CORPORATION, Hsinchu County (TW)

(72) Inventors: Wen-Chi Cheng, Hsinchu County (TW); Guan-Yu Lin, Hsinchu (TW); Yao-Peng Xue, Hsinchu (TW); Chung-Yu Lan, Hsinchu (TW); Frank Lin, Hsinchu County (TW)

(73) Assignee: General Biologicals Corporation, Hsinchu (TW)

( * ) Notice: Subject to any disclaimer, the term of this patent is extended or adjusted under 35 U.S.C. 154(b) by 0 days.

(21) Appl. No.: 15/642,422

(22) Filed: Jul. 6, 2017

(65) Prior Publication Data

US 2017/0319654 A1    Nov. 9, 2017

Related U.S. Application Data

(63) Continuation-in-part of application No. 15/498,482, filed on Apr. 27, 2017, now Pat. No. 9,856,302, which is a continuation-in-part of application No. 15/175,011, filed on Jun. 6, 2016, now abandoned.

(60) Provisional application No. 62/196,292, filed on Jul. 23, 2015.

(51) Int. Cl.
*A61K 38/00* (2006.01)
*A61K 38/16* (2006.01)
*A61K 38/17* (2006.01)
*C07K 14/00* (2006.01)
*C07K 14/47* (2006.01)
*C07K 14/435* (2006.01)

(52) U.S. Cl.
CPC ...... *A61K 38/1709* (2013.01); *A61K 38/1729* (2013.01); *C07K 14/4723* (2013.01)

(58) Field of Classification Search
CPC .... A61K 38/00; A61K 38/16; A61K 38/1709; A61K 38/17; C07K 14/435; C07K 14/4723; C07K 14/00; C07K 14/47
USPC ......... 530/326, 324, 325; 514/2.3, 2.4, 21.3, 514/21.4
See application file for complete search history.

(56) References Cited

U.S. PATENT DOCUMENTS

| 8,754,039 B2 * | 6/2014 | Eckert | A61K 8/64 |
| | | | 514/2.4 |
| 2011/0039761 A1 * | 2/2011 | Eckert | A61K 8/64 |
| | | | 514/2.4 |

* cited by examiner

*Primary Examiner* — Julie Ha
(74) *Attorney, Agent, or Firm* — Hannah M. Tien

(57) ABSTRACT

A method for treating a microbial infection in a subject includes administering to the subject a pharmaceutical composition which has a therapeutically effective amount of an antimicrobial peptide containing a derivative of P-113.

16 Claims, 17 Drawing Sheets
(2 of 17 Drawing Sheet(s) Filed in Color)
Specification includes a Sequence Listing.

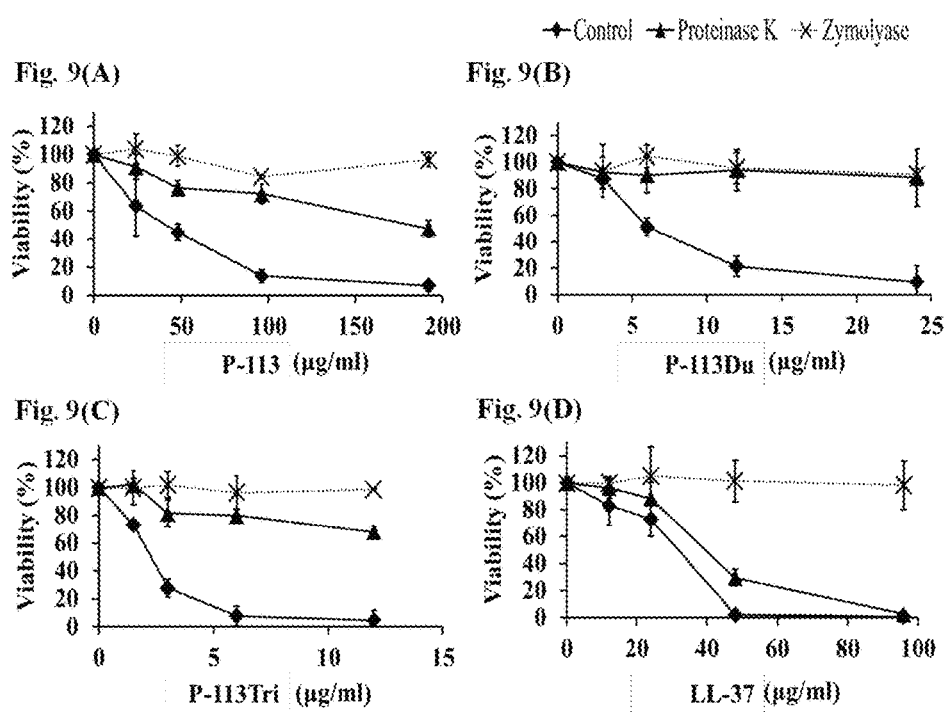

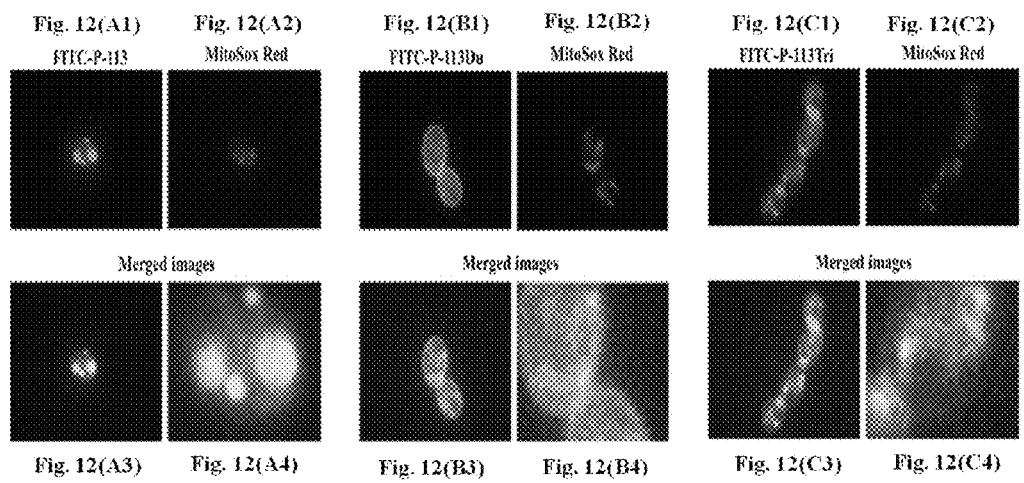

METHOD FOR TREATING MICROBIAL INFECTION

CROSS-REFERENCES TO RELATED APPLICATIONS

This application is a Continuation-in-Part application of the pending U.S. patent application Ser. No. 15/498,482 filed on Apr. 27, 2017, which is a Continuation-in-Part application of the pending U.S. patent application Ser. No. 15/175,011 filed on Jun. 6, 2016, all of which are hereby incorporated by reference in their entireties. Although incorporated by reference in its entirety, no arguments or disclaimers made in the parent application apply to this divisional application. Any disclaimer that may have occurred during the prosecution of the above-referenced application(s) is hereby expressly rescinded. Consequently, the Patent Office is asked to review the new set of claims in view of the entire prior art of record and any search that the Office deems appropriate. The present application claims priority to U.S. Provisional Appl. No. 62/196,292, filed Jul. 23, 2015, which is incorporated herein by reference in its entirety. This application also contains a Sequence Listing in computer readable form. The computer readable form is incorporated herein by reference.

BACKGROUND OF THE INVENTION

Field of the Invention

The present invention provides a method for treating a microbial infection in a subject comprising administering to the subject a pharmaceutical composition comprising a therapeutically effective amount of an antimicrobial peptide containing a derivative of P-113.

Description of Prior Art

Immunocompromised patients are susceptible to opportunistic infections caused by pathogens such as fungus *Candida albicans* or many different types of bacteria. Sometimes these infections cause fetal death. Candidate patients include patients suffering from AIDS (acquired immunodeficiency syndrome), diabetes, kidney disease or xerostomia, and other medications (steroids/chemotherapy for cancer) or physical (pregnancy) state. Once infected, these patients are prone to candidiasis, pneumonia, *Salmonella* infection, or even turn into systemic infection and multiple organ failure. As to the treatment, *Candida albicans* and many pathogens are easy becoming drug resistant to antibiotics.

Histatins, a family of histidine-rich peptides and found in saliva, are secreted by human parotid gland and submandibular gland. At present, about 12 histatins have been discovered. Histatin 1, histatin 3 and histatin 5 are the three major histatins (constitute approximately 70-80% of total histatins), having 38, 32, and 24 amino acids, respectively. These three histatins are highly homologous. Histatin 5 is a proteolytic product of histatin 3. Other histatins are often proteolytically derived from these three major histatins.

These three major histatins exhibit antimicrobial activities against a plurality of oral microbial infections. These histatins, secreted in human body, are capable of blocking the growth of *Candida albicans* in both balstopore and mycelial forms. They have a microbial suppression effect on a wide variety of bacteria, including *Streptococcus mutans, Porphyromonas gingivalis, Actinomyces viscosus*, etc.

Therefore, antimicrobial substances produced by human body can provide effective treatment of microbial infections.

SUMMARY OF THE INVENTION

The present invention provides a method for treating a microbial infection in a subject, comprising administering to the subject a pharmaceutical composition, wherein the pharmaceutical composition comprises a therapeutically effective amount of a peptide comprising the amino acid sequence of SEQ ID NO: 4 or 5.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 shows the effects of salt concentrations and pH values on P-113 and P-113-derived P-113Du and P-113Tri.

FIG. 6 shows the effects of P-113Du and P-113Tri on *C. albicans* biofilm cells.

FIG. 8 shows the images of the location of FITC-labeled antimicrobial peptides (AMPs) in *C. albicans*.

FIG. 9 shows the effects of cell wall disrupting agents on the peptide activity. FIG. 9(A) shows the effects of cell wall disrupting agents on P-113 activity. FIG. 9(B) shows the effects of cell wall disrupting agents on P-113Du activity. FIG. 9(C) shows the effects of cell wall disrupting agents on P-113Tri activity. FIG. 9(D) shows the effects of cell wall disrupting agents on LL-37 activity. Control: no agent; Proteinase K: Proteinase K (1 mg/ml); and Zymolyase: Zymolyase (5 mg/ml).

FIG. 10 shows specific binding of AMPs to laminarin and mannan.

FIG. 11 shows the effect of ochiA mutant on AMPs activity.

FIG. 12 shows FITC labeled AMPs targeting to mitochondria. FIGS. 12(A1) and 12(A2) show the staining results of the FITC-P113 and mitochondria (MitoSox Red), respectively. FIGS. 12(A3) and 12(A4) show the merged images of FIGS. 12(A1) and 12(A2). FIGS. 12(B1) and 12(B2) show the staining results of the FITC-P113Du and mitochondria (MitoSox Red), respectively. FIGS. 12(B3) and 12(B4) show the merged images of FIGS. 12(B1) and 12(B2). FIGS. 12(C1) and 12(C2) show the staining results of the FITC-P113Tri and mitochondria (MitoSox Red), respectively. FIGS. 12(C3) and 12(C4) show the merged images of FIGS. 12(C1) and 12(C2).

FIG. 13 shows that AMPs trigger reactive oxygen species (ROS) formation.

FIG. 14 shows the effects of ROS scavenger on the AMPs activity.

FIG. 15 shows the assay of oxygen consumption of the AMPs activity.

DETAILED DESCRIPTION OF THE INVENTION

Figure 1:
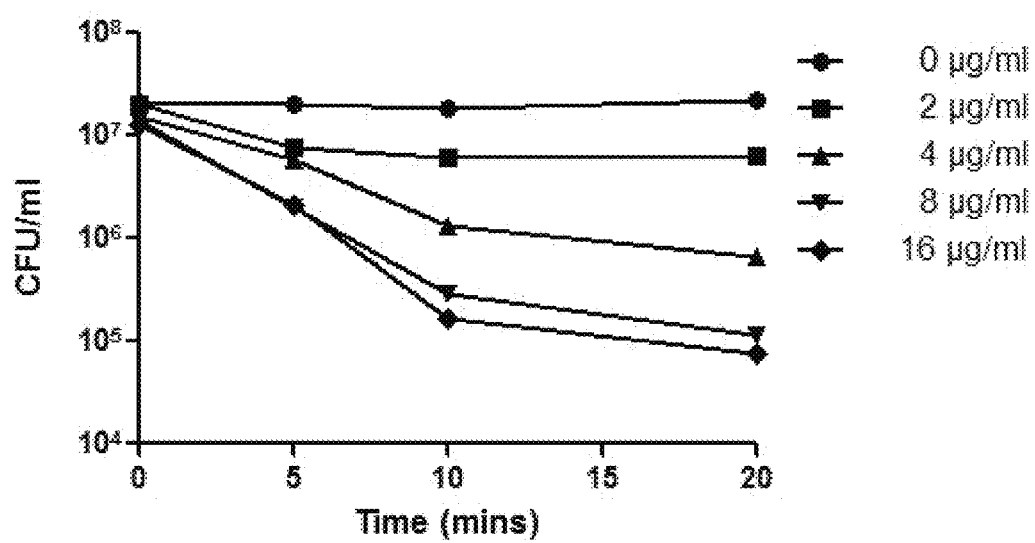
FIG. 1 shows that as the concentration and treating time increase, the antimicrobial activity of peptide P-113 against *Candida albicans* also increases. The experiment is conducted by treating *Candida albicans* cell suspension at 37° C. with different concentrations of P-113. The results represent an average of three independent experiments. CFU: colony-forming unit.

The present invention demonstrates that the antimicrobial activity of the antimicrobial peptide P-113, derived from the sequence of histatin 5, increases as the concentration and treatment time increase and P-113 is effective against drug-resistant clinical strains. Experiments of P-113-derived peptides, P-113Du and P-113Tri (SEQ ID NOS: 4 and 5, respectively), prove that they have α-helical structure and exhibit more effective antimicrobial activities in high-salt environment as compared to the antimicrobial peptide P-113. More importantly, P-113Du and P-113Tri can kill suspension cells of *Candida albicans* more effectively than P-113 can. Accordingly, the present invention proves that P-113 and antimicrobial peptides derived from P-113 have highly potentiated antimicrobial activities against *Candida albicans* infections.

Pharmaceutical compositions comprising peptides are advantageous over antibiotics in many ways, for example, there exist multiple mechanisms for killing bacteria, they can penetrate cell membranes to cause bacterial death, they can also enter the cytoplasm to cause damages to various organelles (mitochondria, DNA in the nucleus, etc.), or they can damage channel proteins, etc., to cause bacterial death. Because of these features, it is difficult for bacteria to develop drug resistance to antimicrobial peptides, thereby greatly increasing the possibility of developing new pharmaceutical compositions from antimicrobial peptides. In addition, antimicrobial peptides are products extracted, purified, modified from the nature (human, animal, plant) with high selectivity, they are much safer and with much less side effects as compared to antibiotics.

However, antimicrobial peptides also have some drawbacks, for example, the peptides is too short to be physically and chemically stable and thus they are readily hydrolyzed, or the antimicrobial peptides lose their antimicrobial activities in a high salt environment or at different pH values because of changes in structure or in electrostatic charges. Therefore, to alleviate these drawbacks and to further enhance the antimicrobial activities of the peptides, the present invention designs P-113Du and P-113Tri. By repeating the sequence of P-113 to elongate the peptides, it is possible to stabilize their physical and chemical properties and to form a more stable secondary structure that is less susceptible to proteolysis in the environment to lose their antimicrobial activities. In addition, P-113Du and P-113Tri also exhibit excellent antimicrobial activities in high salt environments and at different pH values. Therefore, P-113Du and P-113Tri maintain all the advantages of antimicrobial peptides while overcoming the drawbacks associated with the antimicrobial peptides to further enhance their activities for killing microorganisms. They are indeed novel antimicrobial peptides of great potential.

The present invention provides P-113-derived antimicrobial peptides, which comprise P-113-HH, P-113-LL, P-113Du and P-113Tri. The amino acid sequence of P-113-HH comprises SEQ ID NO: 2 or its derivatives, the amino acid sequence of P-113-LL comprises SEQ ID NO: 3 or its derivatives, the amino acid sequence of P-113Du comprises SEQ ID NO: 4 or its derivatives, and the amino acid sequence of P-113Tri comprises SEQ ID NO: 5 or its derivatives.

The term "P-113" used herein is a peptide sequence comprising SEQ ID NO: 1. P-113 (comprising SEQ ID NO: 1) and its derivatives further comprise L form and D form of amino acids, and a peptide sequence of which the amino acid sequence is modified, for example: the C-terminus of the amino acid sequence is modified and the modification is adding $NH_2$ to the C terminus. For example, the C-terminus of SEQ ID NO: 1 is modified with $NH_2$, more specifically, the carboxyl group of the last amino acid of the amino acid sequence is modified with $NH_2$. The preparation of P-113 peptide structure can be found in U.S. Pat. Nos. 5,631,228, 5,646,119, 5,885,965 and 5,912,230, which are hereby incorporated by reference in their entireties.

The term "a" or "an" as used herein is to describe elements and ingredients of the present invention. The term is used only for convenience and providing the basic concepts of the present invention. Furthermore, the description should be understood as comprising one or at least one, and unless otherwise explicitly indicated by the context, singular terms include pluralities and plural terms include the singular. When used in conjunction with the word "comprising" in a claim, the term "a" or "an" may mean one or more than one.

The term "or" as used herein may mean "and/or."

The present invention provides a peptide which comprises the amino acid sequence of SEQ ID NO: 1, wherein the C terminus of the amino acid sequence of SEQ ID NO: 1 is modified with a $NH_2$. Therefore, by modifying the C terminus of SEQ ID NO: 1 with $NH_2$, the microbial suppression effect is significant as compared to the original P-113 peptide, for example, the peptide maintains its antifungal or antibacterial effect in an environment of high salt or high pH value (such as pH 6-9). In addition, the peptide (the C terminus of SEQ ID NO: 1 is modified with $NH_2$) further destructs and kills biofilms formed by bacteria or fungi. In one embodiment, the peptide inhibits biofilm formation by one of action mechanisms, i.e., inhibits bacterial or fungal growth by generating oxygen free radicals.

In one embodiment, the amino acid sequence of SEQ ID NO: 1 is further connected with at least one amino acid sequence of SEQ ID NO: 1. Therefore, when the C terminus of SEQ ID NO: 1 is modified with $NH_2$, the N terminus of SEQ ID NO: 1 is capable of connecting with at least one amino acid sequence of SEQ ID NO: 1.

In another embodiment, a content of an α-helical secondary structure contained in the peptide is at least higher than 1%. Therefore, the content of the α-helical secondary structure contained in the amino acid sequence of SEQ ID NO: 1 is at least higher than 1%. In one embodiment, the content of the α-helical secondary structure contained in the peptide ranges from 1 to 90% or from 1 to 70%. In some embodiments, the content of the α-helical secondary structure contained in the peptide ranges from 2 to 50% or from 2 to 40%.

The present invention also provides a method for treating a microbial infection in a subject, comprising administering to the subject a pharmaceutical composition, wherein the pharmaceutical composition comprises a therapeutically effective amount of a peptide comprising the amino acid sequence of SEQ ID NO: 1, wherein the C terminus of the amino acid sequence of SEQ ID NO: 1 is modified with a $NH_2$.

The term "microbial infection" as used herein may typically refer to that the infection is caused by microorganisms. In one embodiment, the microorganisms are fungi or bacteria.

In one embodiment, the amino acid sequence of SEQ ID NO: 1 is further connected to at least one amino acid sequence of SEQ ID NO: 1. In another embodiment, a content of an α-helical secondary structure contained in the peptide is at least higher than 1%. In one embodiment, the content of the α-helical secondary structure contained in the peptide ranges from 1 to 90% or from 1 to 70%. In some embodiments, the content of the α-helical secondary structure contained in the peptide ranges from 2 to 50% or from 2 to 40%.

In another embodiment, the effective amount of the peptide ranges from 0.001 µg/ml to 2000 µg/ml. In a preferred embodiment, the effective amount of the peptide ranges from 0.01 µg/ml to 1000 µg/ml. In a more preferred embodiment, the effective amount of the peptide ranges from 0.1 µg/ml to 500 µg/ml.

In one embodiment, the fungi comprise *Candida* spp. In a preferred embodiment the *Candida* spp. comprises *Candida albicans*. In a more preferred embodiment, the fungi comprise *Candida albicans*.

In another embodiment, the bacteria comprise *Pseudomonas aeruginosa, Klebsiella pneumoniae, Enterobacter aerogenes,* and *Staphylococcus aureus*.

The present invention provides a peptide, which comprises the amino acid sequence of SEQ ID NO: 4. In a preferred embodiment, the amino acid sequence of SEQ ID NO: 4 is further connected to at least one amino acid sequence of SEQ ID NO. 1. In addition, the C terminus of the SEQ ID NO: 4 is able to be modified with a $NH_2$. Therefore, when the C terminus of the SEQ ID NO: 4 is modified with $NH_2$, the N terminus of the SEQ ID NO: 4 is capable of being connected with at least one amino acid sequence of SEQ ID NO: 1.

When the amino acid sequence of SEQ ID NO: 4 is further connected with at least one amino acid sequence of SEQ ID NO: 1, its content of the α-helical secondary structure is at least higher than 1%. In one embodiment, the content of the α-helical secondary structure contained in the peptide ranges from 1 to 90%, preferably from 1 to 70%, more preferably from 5 to 70%; in another embodiment, the content of the α-helical secondary structure contained in the peptide ranges from 5 to 35%. In some embodiments, the content of the α-helical secondary structure contained in the peptide ranges from 2 to 50%, preferably from 2 to 40%, more preferably from 2 to 35%.

The present invention provides a peptide consisting of the amino acid sequence of SEQ ID NO: 4. In one embodiment, the C terminus of the amino acid sequence of SEQ ID NO: 4 is modified with a $NH_2$. Therefore, the present invention also provides a peptide consisting of the amino acid sequence of SEQ ID NO: 4, wherein the C terminus of the amino acid sequence of SEQ ID NO: 4 is modified with a $NH_2$.

In addition, when the amino acid sequence of SEQ ID No: 4 is further only connected to one segment of amino acid sequence of SEQ ID NO: 1, the amino acid sequence of SEQ ID NO: 5 is thus formed. The present invention provides a peptide consisting of the amino acid sequence of SEQ ID NO: 5. In one embodiment, the C terminus of the amino acid sequence of SEQ ID NO: 5 is modified with a $NH_2$. Therefore, the present invention also provides a peptide consisting of the amino acid sequence of SEQ ID NO: 5, wherein the C terminus of the amino acid sequence of SEQ ID NO: 5 is modified with a $NH_2$.

In one embodiment, the content of the α-helical secondary structure contained in the above peptides (such as a peptide comprising SEQ ID NO: 4 and 5) is at least higher than 1%. In a preferred embodiment, the content of the α-helical secondary structure contained in the peptide is at least higher than 3%. In a more preferred embodiment, the content of the α-helical secondary structure contained in the peptide is at least higher than 5%.

The term "peptide" as used herein may typically refer to a peptide shorter in length. Therefore, peptides, oligopeptides, dimers, multimers and the like are within the scope as defined. The definition intends to cover full-length proteins and fragments thereof. The term "polypeptide" and "protein" also includes post-expression modification of polypeptides and proteins, for example, glycosylation, acetylation, phosphroylation and the like. For purposes of the present invention, "polypeptide" may include "modification" of a native sequence, such as deletion, insertion, substitution (the nature may be conservative or include the following substitution: any one of the 20 amino acids normally found in human proteins, or any other naturally or non-naturally occurring amino acids or atypical amino acids) and chemical modification (insertion of or substitution with mimetic peptides). These modifications may be deliberate or site-directed mutagenesis, or by chemically modifying amino acid to delete or connect chemical moieties, or may be accidental, for example, due to mutation induced by protein-generating hosts or due to mistakes caused by PCR amplifications.

The present invention provides a method for treating a microbial infection in a subject, comprising administering to the subject a pharmaceutical composition, wherein the pharmaceutical composition comprises a therapeutically effective amount of a peptide comprising the amino acid sequence of SEQ ID NO: 4 or 5.

Antimicrobial peptide P-113 is a histatin-5, consisting of 12 amino acids of histatin-5. P-113 comprises the sequence of SEQ ID NO: 1. P-113Du comprises SEQ ID NO: 4 which is composed of two SEQ ID NO: 1 linked together. In another embodiment, the amino acid sequence of SEQ ID NO: 4 is further connected with at least one amino acid sequence of SEQ ID NO: 1. In a more preferred embodiment, when the amino acid sequence of SEQ ID NO: 4 is further connected with a segment of amino acid sequence of SEQ ID NO: 1, the amino acid sequence of SEQ ID NO: 5 is thus formed. P-113Tri comprises SEQ ID NO: 5, which is composed of three segments of amino acid sequence of SEQ ID NO: 1.

The present invention also provides a method for treating a microbial infection in a subject, comprising administering to the subject a pharmaceutical composition, wherein the pharmaceutical composition comprises a therapeutically effective amount of a peptide consisting of SEQ ID NO: 4 or 5.

In one embodiment, the C-terminus of SEQ ID NO: 4 is modified with a $NH_2$. In a preferred embodiment, the C-terminus of SEQ ID NO: 5 is modified with a $NH_2$.

Therefore, the present invention also provides a method for treating a microbial infection in a subject, comprising administering to the subject a pharmaceutical composition, wherein the pharmaceutical composition comprises a therapeutically effective amount of a peptide consisting of the amino acid sequence of SEQ ID NO: 4, wherein the C terminus of the amino acid sequence of SEQ ID NO: 4 is modified with a $NH_2$.

The present invention further provides a method for treating a microbial infection in a subject, comprising administering to the subject a pharmaceutical composition, wherein the pharmaceutical composition comprises a therapeutically effective amount of a peptide consisting of the amino acid sequence of SEQ ID NO: 5, wherein the C terminus of the amino acid sequence of SEQ ID NO: 5 is modified with a $NH_2$.

In another embodiment, a content of an α-helical secondary structure contained in the peptide is at least higher than 1%. In a preferred embodiment, the content of the α-helical secondary structure contained in the peptide is at least higher than 1%. In a more preferred embodiment, the content of the α-helical secondary structure contained in the peptide is at least higher than 5%. Therefore, the content of the α-helical secondary structure contained in the amino acid sequence of SEQ ID NO: 4 or in the amino acid sequence of SEQ ID NO: 4 which is further connected with at least one amino acid sequence of SEQ ID NO: 1 (such as SEQ ID NO: 5) is at least higher than 1%.

In one embodiment, the content of the α-helical secondary structure contained in the peptide ranges from 1 to 90%, preferably from 1 to 70%, more preferably from 5 to 70%; in another embodiment, the content of the α-helical secondary structure contained in the peptide ranges from 5 to 35%. In some embodiments, the content of the α-helical secondary structure contained in the peptide ranges from 2 to 50%, preferably from 2 to 40%, more preferably from 2 to 35%.

In another embodiment, the microbial infections comprise oral infections, vaginal infections, urinary infections, skin infections, eye infections and systemic infections.

The term "treating microbial infection" used herein comprises the treating a fungal infection and/or a bacterial infection. In one embodiment, the term "antifungal or antibacterial" refers to treating the fungal and/or bacterial infection. The term "treating fungal infection" or "antifungal" as used herein includes antifungal properties of various forms, for example, inhibiting the growth of fungal cells, killing fungal cells, or interfering with or impeding fungal life cycles, such as spore germination, sporulation, mating. The term "treating bacterial infections" or "antibacterial" as used herein includes killing bacteria, eliminating bacteria, disinfecting, suppressing bacteria, anti-mildew or anti-mitotic, etc.

The term "bacterium (bacteria)" or "fungus (fungi)" as used herein includes but not limited to: *Candida* spp., *Escherichia coli*, *Actinomyces* spp., *Acinetobacter* spp., *Bacteroides* spp., *Campylobacter* spp., Capnocytophaga spp., *Clostridium* spp., *Enterobacter* spp., *Eikenella* spp., *Eubacterium* spp., *Fusobacterium* spp., *Klebsiella* spp., *Peptostreptococcus* spp., *Porphyromonas* spp., *Prevotella* spp., *Propionibacterium* spp., *Pseudomonas* spp., *Salmonella* spp., *Selenomonas* spp., *Staphylococcus* spp., *Streptococcus* spp., *Treponema* spp., *Veillonella* spp., *Wolinella* spp., as well as drug-resistant strains of various bacteria.

In another embodiment, the fungi comprise *Candida* spp. In a preferred embodiment the *Candida* spp. comprises *Candida albicans, C. tropicalis, C. dubliniensis, C. glabrata, C. guilliermondii, C. krusei, C. lusitaniae, C. parapsilosis, C. pseudotropicalis, C. famata*, and other pathogenic *Candida*. In a more preferred embodiment, the fungi comprise *Candida albicans*.

Therefore, in one embodiment, the fungal infection is a *Candida* infection. In a preferred embodiment, the fungal infection is a *Candida albicans* infection.

In one embodiment, the fungi comprise drug-resistant fungi. In a preferred embodiment, the *Candida* is *Candida* spp. having drug-resistance. In a more preferred embodiment, the *Candida* is *Candida albicans* having drug-resistance. In an even more preferred embodiment, the drug-resistance comprises resistance to fluconazole, resistance to amphoterincin B or resistance to caspofungin etc.

Therefore, in one embodiment, the fungal infection is a drug-resistant fungal infection. In a preferred embodiment, the fungal infection is a drug-resistant *Candida* infection. In a more preferred embodiment, the drug-resistance is resistance to fluconazole, amphoterincin or caspofungin.

In one embodiment, the peptide maintains its antifungal or antibacterial effect in a high salt environment. Thus, P-113Du (SEQ ID NO: 4) and P-113Tri (SEQ ID NO: 5) exhibit better tolerance to environmental stress than P-113 does, i.e., when the peptide comprises more than two SEQ ID NO: 1, the stability has been greatly improved.

In one embodiment, the peptide has an effect for inhibiting fungal growth at pH value ranging from 3 to 10. In a preferred embodiment, the peptide has an effect for inhibiting fungal growth at pH value ranging from 4 to 9. In a more preferred embodiment, the peptide has an effect for inhibiting fungal growth at pH value ranging from 6 to 9.

In another embodiment, the peptide further destructs and kills biofilms formed by bacteria or fungi. In a preferred embodiment, the peptide further treats infections caused by fungal biofilms.

In the present invention, one of the treating mechanisms for microbial infection of the antimicrobial peptide is a destruction of the cell surface of a microorganism. The antimicrobial peptides of the present invention (containing P-113, P-113Du and P-113Tri) exert their cytotoxicity action on the cell wall of a fungus. The antimicrobial peptides are able to interact with proteins and polysaccharides in the cell wall of the fungus for destructing the fungus. In one embodiment, the peptide destructs the cell wall of a fungus to treat the fungal infection. In a preferred embodiment, the peptide interacts with polysaccharides of the cell wall to destruct the cell wall of the fungus. In another embodiment, the polysaccharides comprise laminarin and mannan.

In addition, another treating mechanism of the antimicrobial peptide in the present invention is a generation of reactive oxygen species (ROS) to cause cell damage. The antimicrobial peptides of the present invention (containing P-113, P-113Du and P-113Tri) are able to bind to mitochondria of a microorganism to affect mitochondrial respiratory chain. When the mitochondrial respiratory chain is affected by the antimicrobial peptides, the mitochondria will generate reactive oxygen species (ROS) inducing cell damage to achieve microbial suppression effect. In one embodiment, the peptide induces a generation of reactive oxygen species in a microbial cell to treat the microbial infection. In a preferred embodiment, the peptide binds to mitochondria of the microbial cell to induce the generation of reactive oxygen species.

In another embodiment, the peptide induces a generation of reactive oxygen species in a fungal cell to treat the fungal infection. In a preferred embodiment, the peptide binds to mitochondria of the fungal cell to induce the generation of reactive oxygen species.

One of the microbial suppression mechanisms of the peptide is to achieve its microbial suppression effect by generating oxygen free radicals. In one embodiment, the action mechanism of the peptide is to treat fungal infections by generating oxygen free radicals. In a preferred embodiment, the action mechanism of the peptide is to treat *Candida* infections by generating oxygen free radicals.

In another embodiment, the bacteria comprise *Pseudomonas aeruginosa, Klebsiella pneumoniae, Enterobacter aerogenes*, and *Staphylococcus aureus*. In a preferred embodiment, the bacterial infection is a *Pseudomonas aeruginosa* infection, a *Klebsiella pneumonia* infection, an *Enterobacter aerogenes* infection, or a *Staphylococcus aureus* infection.

The pharmaceutical composition further comprises a pharmaceutically acceptable carrier. The term "a pharmaceutically acceptable carrier" as used herein is determined by the specific combination and the specific method the composition is administered. The term "carrier" as used herein includes but not limited to any and all solvents, dispersing media, vehicles, coatings, diluents, antibacterial and antifungal agents, penetration and absorption delaying agents, buffers, carrier solutions, suspension fluids, colloidal gels, etc.

These media and reagents used as active ingredients of the pharmaceutical composition are well-known in the art. If a conventional medium or reagent is incompatible with any of the active ingredients, care must be taken when it is used in a composition for treatment purposes. Complementary active ingredients may also be incorporated into the composition. The term "pharmaceutically acceptable" as used herein refers to molecular entities and compositions administered to a subject without causing any allergic reactions or similar negative effects. It is conventional and well known in the art to use proteins as active ingredients in water compositions. Typically, the composition is prepared as a liquid solution or a suspension for injections, or prepared in a solid form which is soluble or suspendable for injections.

In one embodiment, the effective amount of the peptide ranges from 0.001 µg/ml to 2000 µg/ml. In a preferred embodiment, the effective amount of the peptide ranges from 0.01 µg/ml to 1000 µg/ml. In a more preferred embodiment, the effective amount of the peptide ranges from 0.1 µg/ml to 500 µg/ml. In another preferred embodiment, the effective amount of the peptide ranges from 1 µg/ml to 50 µg/ml. In a preferred embodiment, the effective amount of the peptide ranges from 1 µg/ml to 30 µg/ml.

The term "an effective amount" used herein is a therapeutic dose which can prevent, decrease, stop or reverse a symptom developed in a subject under specific conditions, or partially, completely alleviates symptoms already exist under specific conditions when the subject begins receiving the treatment.

The peptide (such as a peptide comprising SEQ ID NO: 4 or a peptide comprising SEQ ID NO: 1 the C-terminus of which is modified with $NH_2$) and a pharmaceutically acceptable carrier may be administered to a subject through a number of different routes known in the art. In one embodiment, the peptide (such as a peptide comprising SEQ ID NO: 4 or a peptide comprising SEQ ID NO: 1 the C-terminus of which is modified with $NH_2$) and a pharmaceutically acceptable carrier are administered externally, intravenously, subcutaneously, topically, orally or by muscle or inhalation. The pharmaceutical composition will be delivered to target sites by the digestive system and the circulatory system. In one embodiment, the subject is an animal, preferably a mammal, more preferably a human.

The peptide (such as a peptide comprising SEQ ID NO: 4 or a peptide comprising SEQ ID NO: 1 the C-terminus of which is modified with $NH_2$) and a pharmaceutically acceptable carrier may be prepared by a sterile aqueous solution or a dispersion, an aqueous suspension, an oil emulsion, water in a water-in-oil emulsion, site-specific emulsion, a sustained-release emulsion, a viscous emulsion, a micro-emulsion, a nano-emulsion, a liposome, microparticles, microspheres, nanospheres, nano-particles, micro-mercury and several sustained-release natural or synthetic polymers. The pharmaceutically acceptable carrier and P-113 modified peptide may also be prepared as aerosols, tablets, pills, capsules, sterile powders, suppositories, lotions, creams, ointments, pastes, gels, hydrogels, sustained delivery devices, or other formulations which may be used for drug delivery.

EXAMPLES

The examples below are non-limiting and are merely representative of various aspects and features of the present invention.

Example 1

Preparation of P-113, P-113 Derivatives, Modified P-113 and Peptide Derivatives

P-113 originated from histatin-5. P-113 comprises 12 functional amino acid fragments from histatin-5 and the amino acid sequence of P-113 is set forth in SEQ ID NO: 1. The preparation referred to U.S. Pat. Nos. 5,631,228, 5,646,119, 5,885,965, and 5,912,230, all of which were hereby incorporated by reference in their entireties.

The $NH_2$-end on the C-terminus of P-113 which had 12 amino acids was modified by using a peptide synthesizer. P-113 was synthesized according to the standard Fmoc-based solid-phase peptide synthesis and prepared in the peptide synthesizer. The synthesized peptide was purified by reversed phase high performance liquid chromatography (RP-HPLC).

After purification, the present invention employed two enzyme systems, peptidylglycine alpha-monooxygenase (PAM) and peptidylamidoglycolate lyase (PGL), to seal the amino group on the C-terminus of P-113. Monooxygenase first catalyzed to form an alpha-hydroxyglycine derivative which was a glycine-extended precursor, PAM products were then catalyzed by lyase to form amidated peptide and glyoxylate via degradation.

Modified P-113 peptides were synthesized by chemical reactions using P-113 as the basis or prepared by a recombinant DNA comprising mutated nucleic acid sequences. Four modified P-113 peptides were prepared in the present invention: P-113-HH (SEQ ID NO: 2), P-113-LL (SEQ ID NO: 3), P-113Du (SEQ ID NO: 4) and P-113Tri (SEQ ID NO: 5). The C-termini of the above described peptides were modified with $NH_2$ and these modified peptides were used in the present invention to conduct the following experiments.

Example 2

The Anti-*Candida* Activity of P-113 Peptide Showed Time-Dependent and Dose-Dependent Effects
Method:
To examine the activity of P-113 for killing fungus, fungal suppression assays were carried out at various concentrations or reaction times. *Candida albicans* strain SC5314 (wild type, WT) was cultivated in the Yeast extract Peptone Dextrose medium (YPD medium) at 30° C. overnight, transferred to 5 ml of fresh YPD culture broth, and then cultivated again for another 5 hours. After fungi were collected by centrifugation, the fungi were washed with 12.5 mM sodium acetate (NaOAc) twice, redissolved in each well of a 96-well plate with 12.5 mM NaOAc ($1.5 \times 10^6$ cells in 0.1 ml of 12.5 mM NaOAc). Then, the fungi were treated with different concentrations of P-113 for different reaction times at 37° C. Around 4 ml of Phosphate-buffered saline (PBS) was added into each well, took 25 μl of liquid fungi suspension out and inoculated on a solid YPD medium, after being cultivated at 30° C. for 24 hours, the number of colonies were counted.

Result:

As shown in FIG. 1, the cell survival rate decreased, which correlated to an increased concentration of P-113 and a prolonged co-cultivation time. The results show anti-*Candida* activity of P-113 was time-dependent and dose-dependent effects.

Example 3

P-113 was Effective Against Clinical Isolates of Drug-Resistant *Candida*.

The antimicrobial activities against clinical isolates and drug-resistant strains of P-113 and its derived peptides were examined. The present invention evaluated the effect of P-113 on 15 clinical isolates of fungi belonging to the genus *Candida* (see Table 1). Clinical isolates were cultivated overnight at 30° C. under shaking in a YPD cultural broth (1% yeast extract, 2% peptone and 2% glucose), cells were centrifuged and washed with YPD, then cultivated again in a YPD culture broth allowing to grow for 5 hours (initial optical density at 600 nm [$OD_{600}$]~0.5). Cells were washed with PBS and then collected by centrifugation, redissolved in a culture broth (modified RPMI 1640 medium, LYM), the cell concentration was adjusted to ~0.1 [$OD_{600}$]/ml and then treated with P-113. After the mixed solution was cultivated under shaking at 37° C. and 5% $CO_2$ for 24 hours, absorbance measurement (OD value) was performed to determine the minimum inhibitory concentration (MIC).

TABLE 1

Clinical Isolates of *Candida* spp.

| No. | Candida | Minimum Inhibitory Concentration (μg/ml) | | |
|---|---|---|---|---|
| | | P-113 | P-113Du | P-113Tri |
| 1 | C. albicans | 6.25 | 1.56 | 1.56 |
| 2 | C. albicans | 12.50 | 0.78 | 1.56 |
| 3 | C. glabrata | >50.00 | >25.00 | >25.00 |
| 4 | C. krusei | 12.50 | 3.10 | 3.10 |
| 5 | C. parapsilosis | 0.78 | 0.78 | 0.78 |
| 6 | C. tropicalis | 0.78 | 1.56 | 1.56 |
| 7 | C. albicans | 12.50 | 0.78 | 0.78 |
| 8 | C. albicans | 6.25 | 0.78 | 1.56 |
| 9 | C. albicans | 0.78 | 0.78 | 0.78 |
| 10 | C. dubliniensis | 6.25 | 3.10 | 3.10 |
| 11 | C. glabrata | 25.00 | 25.00 | 12.50 |
| 12 | C. krusei | 6.25 | 1.56 | 1.56 |
| 13 | C. tropicalis | 0.78 | 0.78 | 0.78 |
| 14 | C. tropicalis | 0.78 | 0.78 | 0.78 |
| 15 | C. tropicalis | 1.56 | 1.56 | 3.10 |

Example 4

Figure 2:
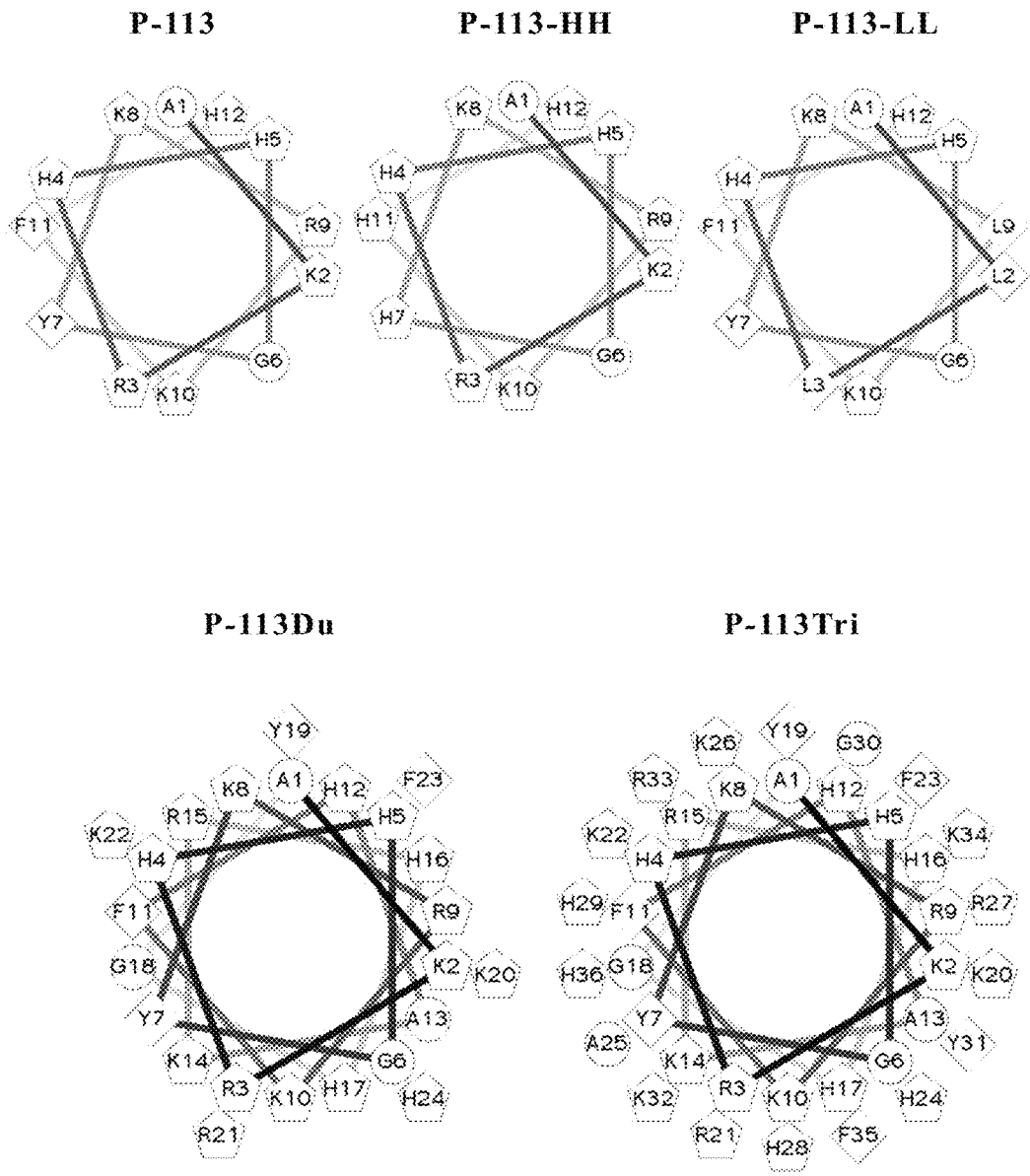
FIG. 2 shows helical-wheel projections of P-113 and antimicrobial peptides derived from P-113. Different shapes represent amino acids having different characteristics, round, diamond, triangle, and pentagon represent hydrophilic, hydrophobic, positively charged and negatively charged amino acids, respectively. In addition, F11, Y7, L9, L2, Y19, F23, Y31 and F35 represent hydrophobic amino acids, G6, G18 and G30 represent lowly hydrophilic amino acid, A1, A13 and A25 represent highly hydrophilic amino acid, and H4, K8, H12, H5, R9, K2, R3, K10, H11, H7, H16, H28, K20, K32, H24, H36, H17, H29, R21, R33, K14, K26, R15, R27, K22 and K34 represent electrically charged amino acids.

Characteristics of P-113-Derived Peptides
Method:
By altering the sequence characteristics of P-113, the antimicrobial activity against *Candida* was improved and several P-113 derivatives were thus designed and synthesized. The ratio of hydrophobic amino acids and net electrical charge of these derivatives were predicted by an Antimicrobial Peptide Database (APD). The helical wheel representing the proteins (http://aps.unmc.edu/AP/main.php) was made by using helical wheel projections (http://rzlab.ucr.edu/scripts/wheel/wheel.cgi).
Result:
The results were shown in Table 2. To enhance the antimicrobial activity of P-113 against *Candida albicans*, the present invention synthesized P-113 derivatives and examined their antimicrobial activities against *Candida* spp. The results showed that P-113-HH had higher hydrophobicity and lower amphiphilic properties as compared to P-113, but P-113-LL had higher hydrophobicity and higher amphiphilic properties as compared to P-113. In addition, P-113Du and P-113Tri carried higher positive valence than P-113 did. FIG. 2 shows helical wheels of P-113 and its derivatives.

TABLE 2

Sequences and characteristics of P-113 peptide and its derivatives

| Peptides | Sequence | Hydorphobicity Ratio | Positive charge |
|---|---|---|---|
| P-113 | AKRHHGYKRKFH-NH$_2$ | 16% | +5 |
| P-113-HH | AKRHHGHKRKHH-NH$_2$ | 8% | +5 |
| P-113-LL | ALLHHGYKLKFH-NH$_2$ | 41% | +2 |
| P-113Du | AKRHHGYKRKFHAKRHEIGYKRKFH-NH$_2$ | 16% | +10 |
| P-113Tri | AKRHHGYKRKFHAKRHHGYKRKFHAKRHEIGYKRKFH-NH$_2$ | 16% | +15 |

Example 5

Figure 3:
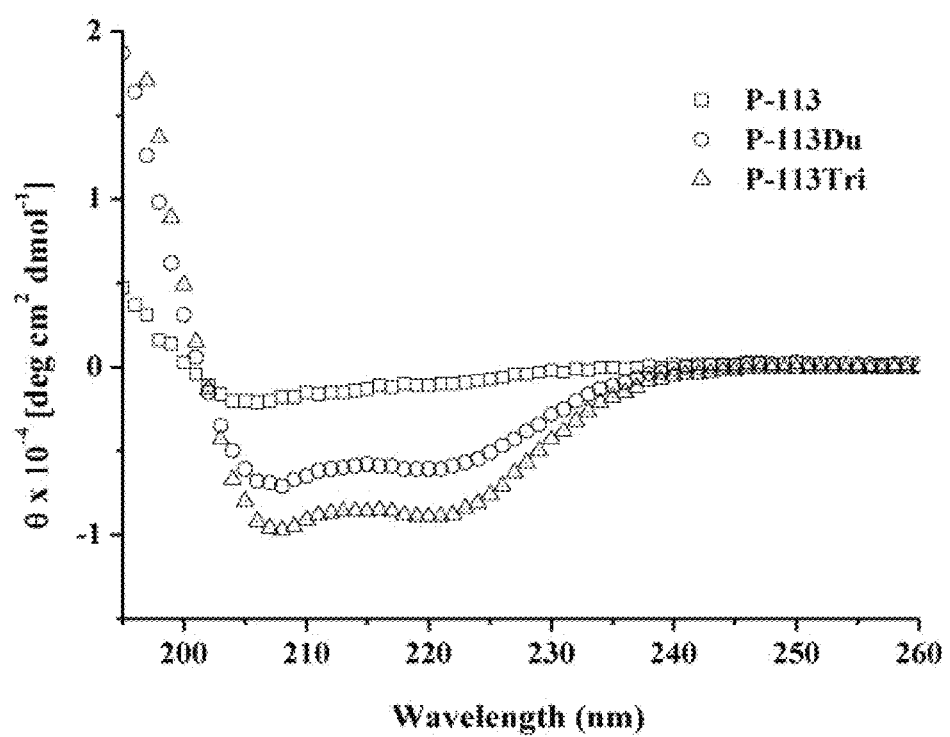
FIG. 3 shows the secondary structure of P-113 and P-113-derived P-113Du and P-113Tri measured in 85% trifluoroethanol solution (TFE, pH 6.0) at 25° C. by a Circular Dichroism Spectrometer. The mean residue molar ellipticity (θ) of P-113, P-113Du and P-113Tri are analyzed over the wavelength range of 195-260 nm with readings every 1 nm.

Secondary Structures of P-113 and its Derivatives
Method:
The present invention utilized a Circular Dichroism Spectrometer (AVIV Company) to observe the secondary structure of the antimicrobial peptides. Circular dichoism spectra of P-113 and its derivatives were recorded over the wavelength range of 195-260 nm with readings every 1 nm by using a quartz cuvette having 1 mm optical path length.
Ellipticities were represented as mean residue molar ellipticity (MRE). P-113, P-113Du and P-113Tri were dissolved in 85% trifluoroethanol (TFE) solution.
Result:
As shown in FIG. 3, P-113, P-113Du and P-113Tri all had α-helical structures. P-113, P-113Du and P-113Tri all had one positive peak at 195 nm and two negative peaks at 208 and 222 nm, which showed that the α-helical secondary structure was generated. When analyzed by BeStSel, the content of the α-helical secondary structure of P-113 was 2.9%, the content of the α-helical secondary structure of P-113Du and P-113Tri were 10.6% and 21.4%, respectively, and the higher content of the α-helical secondary structure represent the peptide had the better and more stable α-helical secondary structure. P-113Tri had the most obvious and stable α-helical structure in the P-113 and P-113 derivatives. P-113Tri was capable of connecting with the cell membrane of bacteria to provide an improved antimicrobial effect. Thus, P-113Tri had the best activity for suppressing microorganism.

Example 6

Figures 4A, 4B:
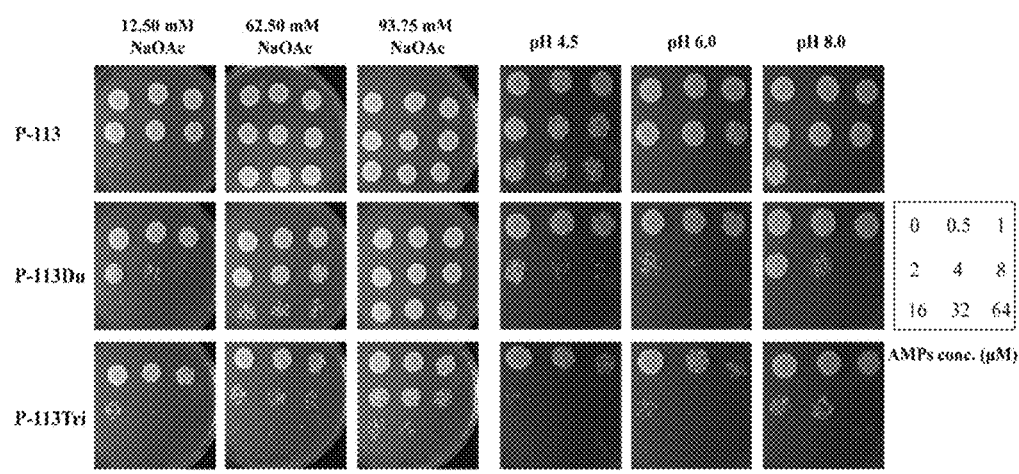
FIG. 4(A) shows that P-113, P-113Du and P-113Tri are dissolved in different concentrations (12.5, 62.5 and 93.75 mM) of sodium acetate solution (NaOAc) and *Candida albicans* is treated with different concentrations of P-113, P-113Du and P-113Tri at 37° C. for one hour.
FIG. 4(B) shows the results of *Candida albicans* after being treated at different pH values and then cultivated in a YPD medium for 1 day. Different concentrations of antimicrobial peptides (AMPs conc.) are represented by the numbers shown in the right box.

Method:
Salt Tolerance of P-113 and its Derivatives
Wild type (WT) *Candida albicans* was cultivated in a YPD medium at 30° C. overnight and then transferred to 5 ml of fresh YPD culture broth, cultivated subsequently for another 5 hours. After the fungi were collected by centrifugation, washed with 12.5 mM sodium acetate twice, redissolved with 12.5 mM NaOAc to yield a fungal concentration of 1.5×10$^6$ cells/ml. Fifty microliters of liquid fungal suspension was taken out to mix with 50 μl of sequentially diluted antimicrobial peptides and placed in different wells of a 96-well plate allowing to react for 1 hour at 37° C. (as shown in FIG. 4(A). Then, 50 μl of liquid fungal mixture was taken out and 450 μl PBS was added to terminate the reaction. Finally, 25 μl was taken out and inoculated on a solid YPD medium.
Result:
The interaction between antimicrobial peptides and the cell membrane of *Candida albicans* was affected by salt concentration. In the high salt environment, the antimicrobial peptides were not easy to interact with cell membrane, and lose its antimicrobial activity. In the other hand, pH value also affected the structural folding of antimicrobial peptides and their antimicrobial activities. These antimicrobial peptides may lose their antimicrobial activities because of the different pH values. Therefore, the present invention examined the salt tolerance and antimicrobial activity of P-113Du and P-113Tri at a high salt environment and different pH values to improve their salt tolerance and antimicrobial activity in different environments, allowing subsequent clinical drug research and development possible.
The results, as shown in FIG. 4(A), indicated that P-113Tri maintained strong antifungal activity in the high salt environment (62.5 and 93.75 mM). P-113 exhibited candidacidal activity in the presence of 12.5 mM sodium acetate but reduced activity in the presence of 62.25 and 93.75 mM salt. However, P-113Du and P-113Tri exhibited potent candidacidal activity even in the presence of 93.75 mM sodium acetate. The results suggested that P-113Du and P-113Tri were able to maintain their antifungal activity in a high salt environment.
The results, as shown in FIG. 4(B), P-113 exhibited candidacidal activity at pH 6 and 8, and the activity was lost at pH 4.5. In contrast, P-113Du and P-113Tri exhibited consistent candidacidal activity at pH 4.5, 6, and 8. These results suggested that P-113Du and P-113Tri are more resistant to high salt and low pH levels than P-113.

Example 7

Antimicrobial Activities of P-113 and its Derivatives Against *Candida albicans*
Method:
Wild type (WT) *Candida albicans* was cultivated in a YPD medium at 30° C. overnight and then transferred to 5 ml of fresh YPD culture broth, subsequently cultivated for another 5 hours. After being collected by centrifugation, the fungi were washed with sodium acetate (12.5 mM) twice, redissolved with 12.5 mM sodium acetate to yield a fungal concentration of $1.5 \times 10^5$ cells/ml. 50 µl of liquid fungal suspension was taken out to be mixed with 50 µl of sequence-diluted antimicrobial peptide and placed in different wells of a 96-well plate, allowing to react (37° C.) for 1 hour (as shown in FIG. 4(A)). Then, 20 µl of fungal liquid mixture was added into 780 µl of PBS to terminate the reaction. Finally, 50 µl was taken out and inoculated on a solid YPD medium, cultivated at 30° C. for 24 hours, then the number of colonies were counted.

Figure 5:
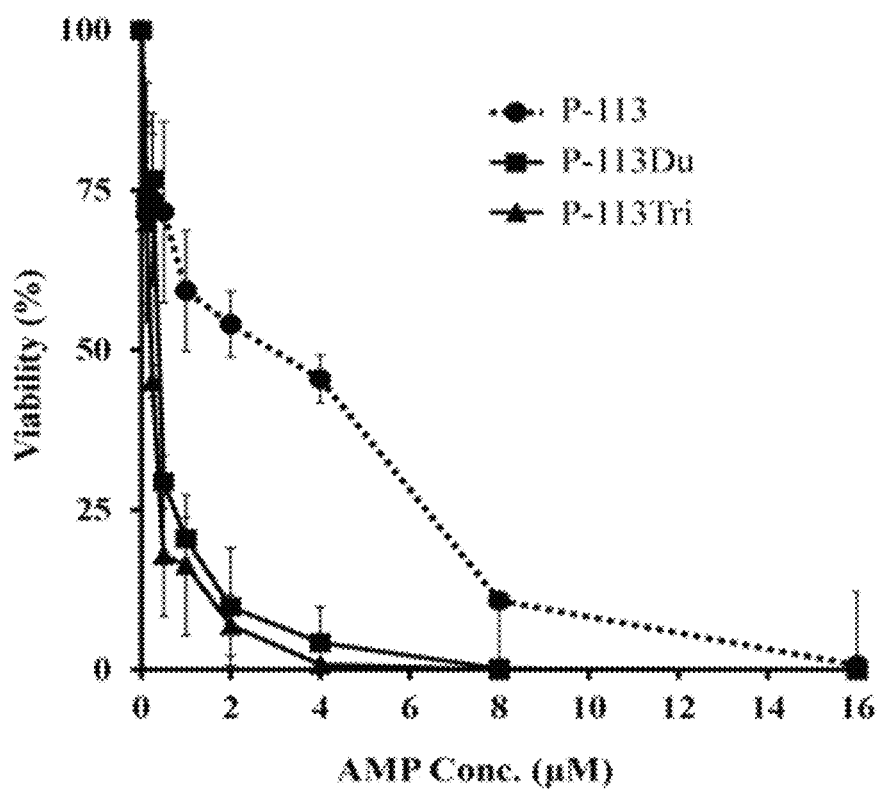
FIG. 5 shows the candidacidal activities of P-113 and P-113-derived P-113Du and P-113Tri against *Candida albicans* cell suspension. *Candida albicans* are treated with different concentrations of P-113, P-113Du and P-113Tri at 37° C. for 1 hour. The results represent an average of three independent experiments. AMP conc.: the concentration of antimicrobial peptide.

Result:

As shown in FIG. 5, P-113Tri and P-113Du exhibited stronger activity for killing fungus than P-113 did.

Example 8

Antifungal Activities of P-113 and its Derivatives Against *Candida albicans* Biofilms Another serious infection problem was the formation of microbial biofilm. Biofilms had been found to be involved in many infections in the human body and implicated infections, such as bacterial vaginosis, urinary tract infections, catheter infections, dental plaque, gingivitis, coating contact lenses and other lethal conditions, such as endocarditis, infections in cystic fibrosis, and infections of permanent indwelling devices, such as joint prostheses and heart valves.

The biofilm was a three-dimensional structure formed when microorganisms gather together. The formation process could be roughly divided into three parts. At first, micro-organisms attached to a substance. Second, microorganisms grew into a mycelium network made up of hyphae and formed an opaque layer covering the surface of the substance. Finally, a large number of extracellular matrix were formed covering the surface of the microorganisms.

Method:

*Candida albicans* strain SC5314 was cultivated in a YPD medium overnight and then transferred to a fresh YPD culture broth, diluted until the concentration was $3 \times 10^5$ cells/ml. 100 µl of liquid fungal suspension was placed in a 96-well plate for cultivation at 37° C. for 24 hours, formed biofilms were washed with sodium acetate (12.5 mM). Then, sequence-diluted antimicrobial peptides P-113, P-113Du and P-113Tri (0-200 µM) were added, reacted at 37° C. for 1 hour, washed with PBS twice. The cellular activity of the biofilms was determined by using XTT (2,3-bis(2-methoxy-4-nitro-5-sulfophenyl)-2H-tetrazolium-5-carboxanilide) reduction assays to analyze the cell survival rate. To perform this reaction, XTT (0.5 mg/ml) and Menadione (0.5 µM) were dissolved in PBS and then added into a 96-well plate formed by biofilms, reacted at 30° C. for 30 minutes, the optical density was measured at wavelength 490 nm ($OD_{490}$). The cellular activity of the biofilms was represented as a percentage.

Biofilms were cultivated in a multi-well plate. After P-113, P-113Du and P-113Tri were added, the biofilms were observed by using a scanning electron microscopy (SEM).

Figures 6A, 6B:
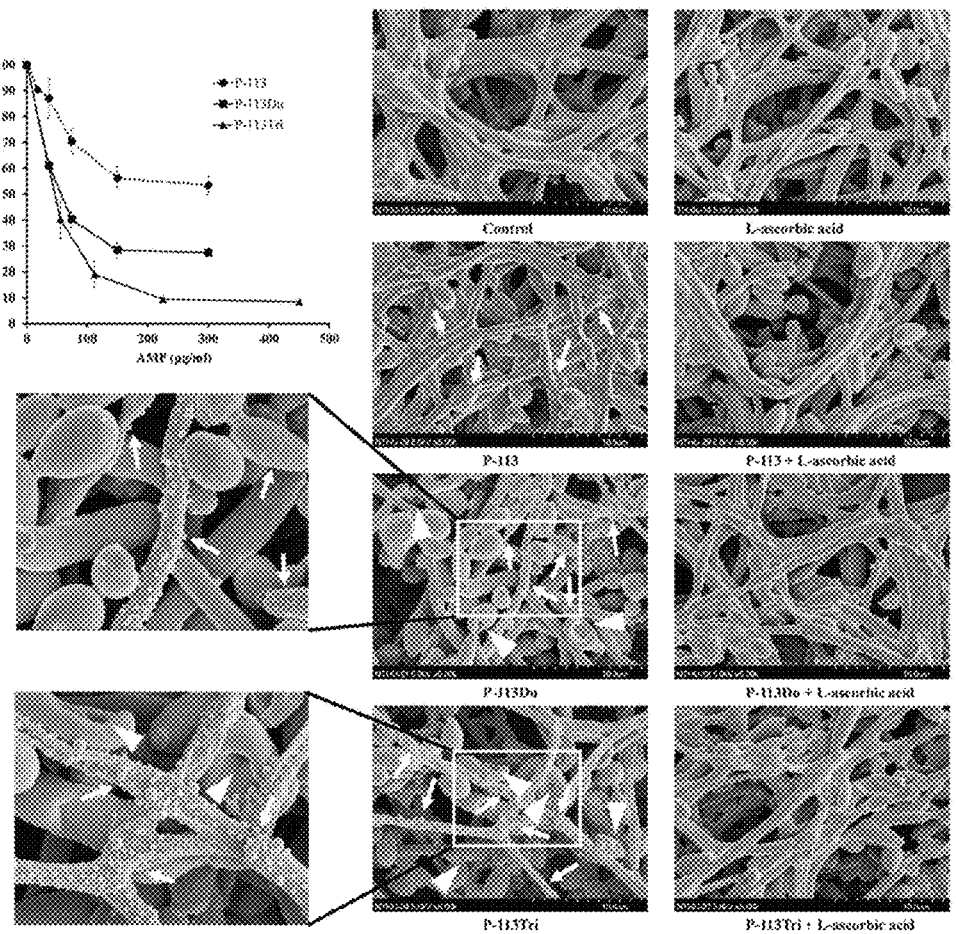
FIG. 6(A) shows viability of biofilm cells with peptide treatment. Biofilms are treated with or without the indicated concentrations of peptides at 37° C. for 1 hr. The experiments are initially performed using 0 to 200 M for P-113 and 0 to 100 M for P-113Du and P-113Tri, expressed as micrograms per milliliter. For example, 100 μM is 150 μg/ml, 300 μg/ml, and 450 μg/ml for P-113, P-113Du, and P-113Tri, respectively. Cell viability is determined by measuring metabolic activity using the XTT reduction method. The data are represented as the mean values±standard deviations (SDs) of three independent experiments.
FIG. 6(B) shows morphology of biofilm cells. Biofilm cells are treated with 50 μM peptides (75 μg/ml, 150 μg/ml, and 225 μg/ml for P-113, P-113Du, and P-113Tri, respectively) and examined by scanning electron microscopy at a magnification of ×5,000. The morphology of the biofilm cells treated with P-113Du and P-113Tri is also examined with a magnification of ×10,000. L-ascorbic acid (final concentration, 1 M) diminishes the rough appearance of protuberances induced by P-113Du and P-113Tri treatments. Arrows point to the rough appearance of protuberances. Triangles point to disc-like depressions.

Results:

Biofilms were related to *C. albicans* infection, and currently available antifungal agents had demonstrated minimal activity against *C. albicans* biofilms. Therefore, the present invention was interested in assessing the activity of P-113Du and P-113Tri against biofilm cells. Biofilms were formed in microtiter wells as previously described and incubated with specific peptide concentrations. The viability of biofilm cells was determined by XTT reduction assay. The metabolic activity of biofilm cells with peptide treatment was normalized to that of control cells (no peptide treatment) and reported as a percentage. P-113Tri exhibited the highest killing activity against biofilm cells, followed by P-113Du and P-113 (FIG. 6A). The concentrations of the peptides causing 50% reduction in the metabolic activity (50% RMA) of the cells were also calculated as previously described. The 50% RMAs of P-113, P-113Du, and P-113Tri were >300, 51.54, and 43.245 µg/ml, respectively.

There were many channels in the biofilm allowing the flow of water and nutrients and the disposal of waste products. The surface of the biofilm was covered with extracellular matrix, enabling the microorganisms to resist agents and attacks from immune system to enhance their viability. Biofilms appeared to be distinct from other infections that were responsible for antibiotic resistance. The results of the present invention indicated that P-113, P-113Du and P-113Tri had an effective activity of suppressing biofilm formation, among which P-113Tri exhibited the best microbial suppression activity.

The effect of the peptides on biofilm cell morphology was also examined by scanning electron microscopy (SEM). In the control (no peptide treatment), the observed cell surfaces were smooth. However, the surfaces of peptide-treated biofilm cells exhibited a rough appearance with protuberances (FIG. 6B). Similar morphologies were observed when *Candida* cells were exposed to miconazole and allyl alcohol. This cellular appearance was previously thought to correlate with the generation of reactive oxygen species (ROS). To test this possibility, biofilm cells were incubated with L-ascorbic acid, a scavenger of ROS, together with 50 µM peptides (75 µg/ml, 150 µg/ml, and 225 µg/ml for P-113, P-113Du, and P-113Tri, respectively) at 37° C. for 1 h. The results of the present invention showed that the extent of protuberance on the cell surface was significantly reduced in the presence of L-ascorbic acid (FIG. 6B).

Moreover, disc-like depressions were also present on the surfaces of the cells during P-113Du and P-113Tri treatment but not during P-113 treatment (FIG. 6B). Cellular depressions were previously shown to reflect the penetration of an antimicrobial substance across the plasma membrane and cytosolic leakage. Distinct surface appearances suggested that P-113Du/P-113Tri and P-113 exert different mechanisms for the killing of *C. albicans*.

Example 9

The Effect of L-Ascorbic Acid on the Antimicrobial Pepetides

Method:

The effect of L-ascorbic acid on the candidacidal activity of P-113, P-113Du and P-113Tri against planktonic cells. Biofilm cells were treated with or without the indicated concentrations of peptides in the presence or absence of L-ascorbic acid (final concentration 50 mM). The mixtures were incubated at 37° C. for 1 h. Cell viability was determined by measuring the metabolic activity using the XTT reduction method as described above. The data were represented as the mean values±SD of three independent experiments.

Figure 7:
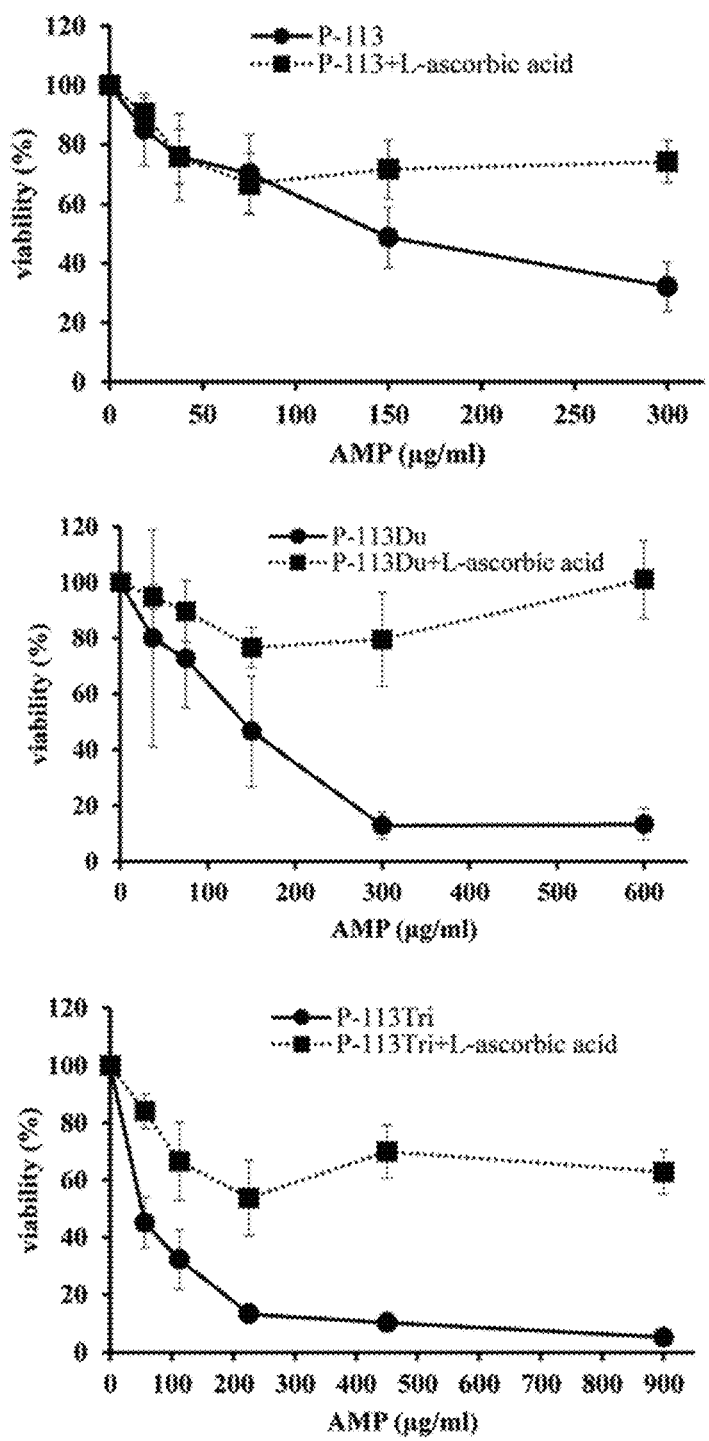
FIG. 7 shows the effect of L-ascorbic acid on the candidacidal activity of P-113, P-113Du, and P-113Tri against biofilm cells. Biofilm cells are treated with or without the indicated concentrations of peptides in the presence or absence of L-ascorbic acid (final concentration, 1 M). The data are represented as the mean values with SD of three independent experiments.

Result:

As shown in FIG. 7, the activities for killing fungus in P-113, P-113Du and P-113Tri against the suspension cells were affected by L-ascorbic acid. The effects of above antimicrobial peptides were compensated by the addition of L-ascorbic acid, significantly decreasing their microbial suppression effects. The results showed that one of the possible action mechanisms of the antimicrobial peptides to suppress *Candida albicans* is through the production of oxygen free radicals.

The activities for killing fungus were also observed when different concentrations of the peptides and L-ascorbic acid were not added. The cell survival rate was determined by using XTT assays. The results were the average of three independent experiments. The results showed that L-ascorbic acid enhanced the viability of the biofilm cells during peptide treatments.

Example 10

Antimicrobial Effects of P-113Du and P-113Tri Against Bacteria

Method:

Wild type (WT) *Pseudomonas aeruginosa, Klebsiella pneumoniae, Enterobacter aerogenes, Staphylococcus aureus* were cultivated overnight in LB medium at 37° C., then transferred to 5 ml of fresh LB culture broth, cultivated again for another 3 hours. Bacteria were collected by centrifugation, washed with sodium acetate (12.5 mM) twice, redissolved with 12.5 mM sodium acetate until the concentration was $1.5 \times 10^5$ cells/ml. Mixed with sequential-diluted anti-bacterial peptides, seeded in different wells of a 96-well plate allowing to react for 1 hour. Then, 20 µl of liquid bacterial mixture was taken out to mix with 780 µl of PBS (Phosphate-buffered saline) to terminate the reaction. 50 µl was then taken out and inoculated on a solid medium, after being cultivated at 30° C. for 24 hours, formed colonies were observed.

Result:

As shown in Table 3, P-113Du and P-113Tri effectively suppressed the growth of *Pseudomonas aeruginosa, Klebsiella pneumoniae, Enterobacter aerogenes*, and *Staphylococcus aureus*.

TABLE 3

Antimicrobial effects of P-113Du and P-113Tri against bacteria

| Bacterial species | Source of bacterial strain | Minimum Inhibitory Concentration (MIC: µg/ml) | |
|---|---|---|---|
| | | P-113Du | P-113Tri |
| Pseudomonas aeruginosa | PAO1, ATCC 15692 | 3.125 | 3.125 |
| Klebsiella pneumoniae | CG43 | 12.5 | 6.25 |
| Enterobacter aerogenes | ATCC 13048 | 25 | 12.5 |
| Staphylococcus aureus | ATCC 33591 | 25 | 25 |

Example 11

Effects of P-113 and its Derivatives on Cells

Method:

To examine the safety of the peptides, human gingival cells (S-G cells) were incubated in DMEM-10% FBS solution and seeded in a 96-well plate for 16 hours at 37° C. Antimicrobial peptides were added and then cultivated for 24 hours, the cell survival rate was then measured by XTT reduction assay.

Result:

The concentration of antimicrobial peptides that caused 50% of cell death were much greater than 400 µg/ml. The results indicated that the antimicrobial peptides were non-toxic to the cells.

Example 12

Confocal Microscopy Images Show the Location of FITC-Labeled P-113, P-113Du and P-113Tri in *C. albicans*

Method:

The SC5314 strain of *Candida albicans* (wild type or WT) were grown overnight in yeast extract peptone dextrose medium (YPD) broth at 30° C. The overnight culture was then subcultured into fresh YPD medium and grown for 5 h. Cells ($1*10^6$ cells) were incubated with FITC-P-113, FITC-P-113Du and FITC-P-113Tri (0.6 µg/ml) for 5 min and 60 min, respectively. The images were obtained using a confocal microscope. Cells were stained with Calcofluor white (8 µg/ml) and incubated with FITC-labeled antimicrobial peptides (AMPs) (0.6 µg/ml) for 5 min.

Figure 8A:
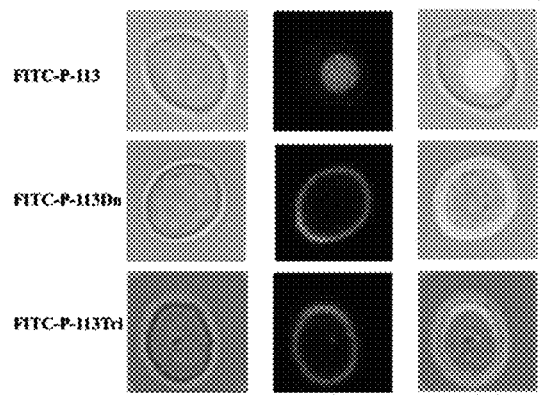
FIG. 8(A) shows the result of the cells (1*10$^6$ cells) incubated with FITC-P-113, FITC-P-113Du and FITC-P-113Tri (0.6 μg/ml) for 5 min.
Figure 8B:
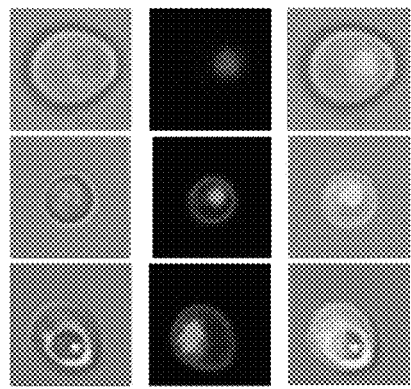
FIG. 8(B) shows the result of the cells (1*10$^6$ cells) incubated with FITC-P-113, FITC-P-113Du and FITC-P-113Tri (0.6 μg/ml) for 5 min.
Figure 8C:
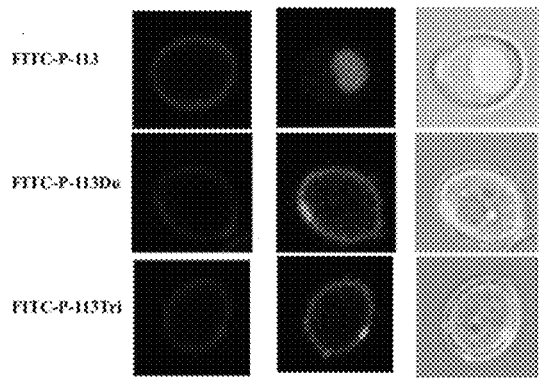
FIG. 8(C) shows the results of the cells stained with calcofluor white (8 μg/ml) and incubated with FITC-P-113, FITC-P-113Du and FITC-P-113Tri (0.6 μg/ml) for 5 min.

Result:

As shown in FIGS. 8(A) and 8(B), exposure to FITC-P-113, FITC-P-113Du and FITC-P-113Tri (0.6 µg/ml) for 60 min revealed different rates and locations of peptide interacting with *C. albicans* cells. The images from the combination of differential interference contrast (DIC) and confocal microscopy showed that FITC-P-113 quickly accumulated inside cells (possibly to be located within vacuoles). However, there were still much FITC-P-113Du and FITC-P-113Tri bound to the cell surface, as demonstrated by staining cell wall with calcofluor white (FIG. 8(C)). These results demonstrated that FITC-P-113Du and FITC-P-113Tri also exerted their cytotoxicity action on the cell surface of *C. albicans*.

Example 13

Effects of Cell Wall Disrupting Agents on the Peptide Activity

Method:

The SC5314 strain of *Candida albicans* (wild type or WT) were grown overnight in YPD broth at 30° C. The overnight culture was then subcultured into fresh YPD medium and grown for 5 h. Cells were treated with Proteinase K (1 mg/ml) for 30 min or Zymolyase (5 mg/ml) for 1 h at 30° C., followed by reacting with different concentrations of the peptides for 1 h, respectively. After that, samples were serially diluted in phosphate-buffered saline (PBS) and 15 µl of each diluent was spotted onto YPD agar plates. Colony-forming units were counted after incubation at 30° C. for 24 h. The data were represented as the mean values±SD of three independent experiments.

Result:

*C. albicans* was surrounded by a cell wall that antifungal peptides must pass through before reaching the plasma membrane and/or cytosol. The present invention thus investigated whether alteration of the cell wall could impact on the candidacidal activity of the peptides. After removal of the outer layer of glycosylated proteins with proteinase K, P-113, P-113Du and P-113Tri failed to kill *C. albicans*. However, the control peptide (LL-37) can still kill *C. albicans* cells treated with proteinase K. Moreover, removal of the β-(1-3)-glucan layer of the cell wall by treatment with Zymolyase also reduced the activity of AMPs (FIGS. 9(A)-9(D)). These results demonstrated that AMPs acted by interacting with cell wall proteins and polysaccharides.

Example 14

Specific Binding of AMPs to Laminarin and Mannan

Method:

The SC5314 strain of *Candida albicans* (wild type or WT) were grown overnight in YPD broth at 30° C. The overnight culture was then subcultured into fresh YPD medium and grown for 5 h. Viability assay was performed by mixing various amounts of *Candida* cell wall components (laminarin and mannan) with different concentrations of peptides for 1 h. After treatment, samples were serially diluted in PBS and 15 μl of each diluent was spotted onto YPD agar plates. Colony-forming units were counted after 24 h incubation at 30° C. The data were represented as the mean values±SD of three independent experiments.

Figure 10A:
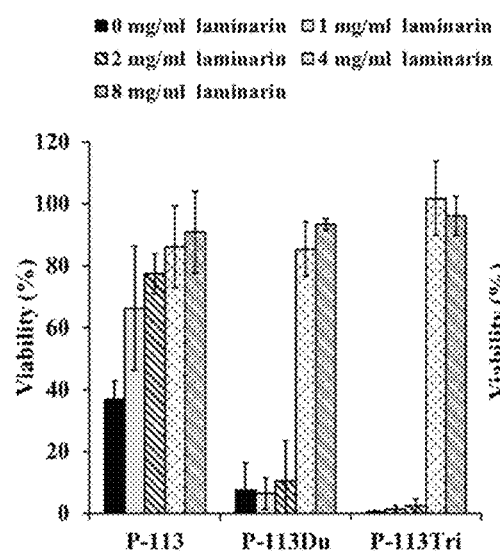
FIG. 10(A) shows the results of the binding of P-113, P-113Du or P-113Tri to laminarin.
Figure 10B:
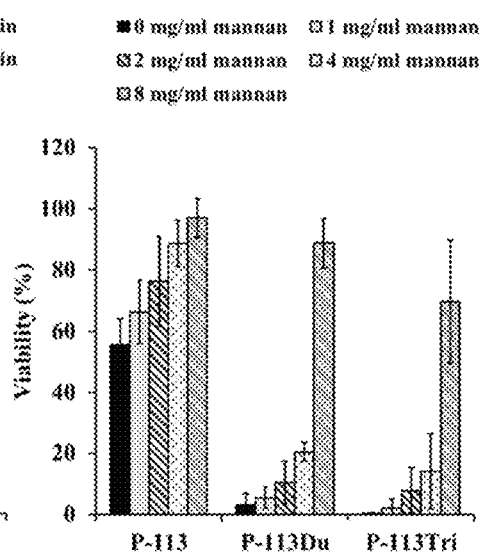
FIG. 10(B) shows the results of the binding of P-113, P-113Du or P-113Tri to mannan.
Figure 11A:
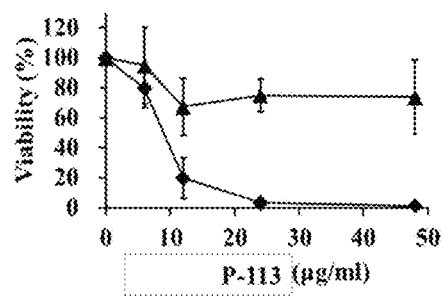
FIG. 11(A) shows the effects of ochiA mutant on P-113 activity.
Figure 11B:
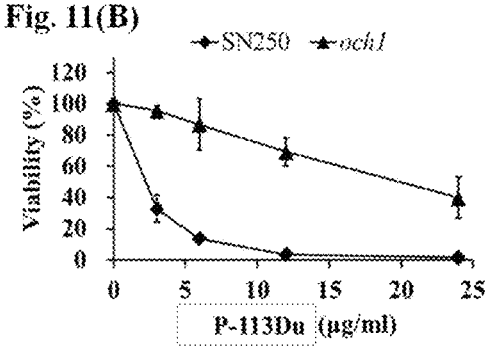
FIG. 11(B) shows the effects of ochiA mutant on P-113Du activity.
Figure 11C:
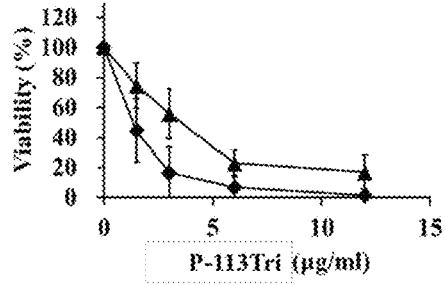
FIG. 11(C) shows the effects of ochiA mutant on P-113Tri activity.
Figure 11D:
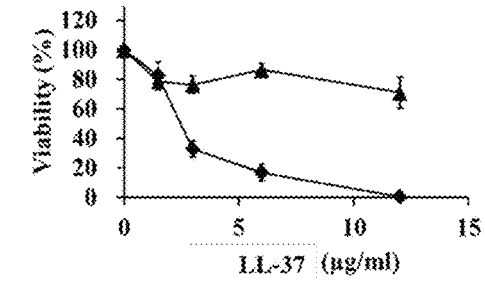
FIG. 11(D) shows the effects of ochiA mutant on LL-37 activity. SN250: SN250 strain; and och1: och1Δmutant strain.

Result:

The present invention investigated the binding of AMPs (containing P-113, P-113Du and P-113Tri) to laminarin or mannan. The activities of all the peptides tested were reduced in proportion to the increasing amount of laminarin and mannan in the mixture (FIGS. 10(A) and 10(B)).

Example 15

The Och1Δ Mutant was Resistant to P-113, P-113Du and LL-37

Method:

The SN250 and och1Δ mutant strains were grown overnight in YPD broth at 30° C. The overnight culture was then subcultured into fresh YPD medium and grown for 5 h. Cells were treated with different concentration of peptides for 1 h. After treatment, samples were serially diluted in PBS and 15 μl of each diluent was spotted onto YPD agar plates. Colony-forming units were counted after 24 h incubation at 30° C. The data were represented as the mean values±SD of three independent experiments.

Result:

Because *Candida albicans* OCH1 gene encodes an alpha-1,6-mannosyltransferase, the OCH1 gene deletion mutant (och1Δ) is defective in N-glycan processing. The och1Δ mutant was resistant to P-113, P-113Du, and LL-37 (the control), whereas the och1Δ mutant was still sensitive to P-113Tri (FIGS. 11(A)-11(D)). These results indicated that N-linked glycosylation of the cell wall carbohydrates were related to AMPs' susceptibility, particularly P-113 and P-113Du.

Example 16

The FITC Labeled AMPs Targeting to Mitochondria

Method:

The SC5314 strain of *Candida albicans* (wild type or WT) were grown overnight in YPD broth at 30° C. The overnight culture was then subcultured into fresh YPD medium and grown for 5 h. Cells ($5*10^7$ cells) were harvested by centrifugation, washed twice with 12.5 mM sodium acetate (NaOAc) and suspended in 200 μl of 12.5 mM NaOAc. The mixture was incubated with 5 μM MitoSox Red at 30° C. for 60 min. Cells were washed twice with NaOAc and harvested by centrifugation. The cell pellets were resuspended in NaOAc to a concentration of $2*10^6$ cells/ml. The FITC-labeled P-113 (1 μM), P-113Du (0.1 μM), and P-113Tri (0.05 μM) were added and the images were taken on a fluorescence microscope (AIX0, Zeiss).

Result:

The result showed the co-localization of FITC labeled AMPs (containing P-113, P-113Du and P-113Tri) with mitochondria (FIGS. 12(A1)-12(C4)). These results raised a possibility that AMPs were mitochondria-targeted.

Example 17

Antimicrobial Peptides P-113, P-113Du and P-113Tri Trigger Reactive Oxygen Species (ROS) Formation Method:

The SC5314 strain of *Candida albicans* (wild type or WT) were grown overnight in YPD broth at 30° C. The overnight culture was then subcultured into fresh YPD medium and grown for 5 h. Cells were harvested by centrifugation, washed twice with 12.5 mM sodium acetate (NaOAc) and resuspended in 12.5 mM NaOAc to a concentration of $1*10^7$ cells/ml. The cells were treated with various AMPs (0.25 μM) for 1 h at 37° C. After treatment, cells were washed twice with 12.5 mM NaOAc. Dihydroethidium (DHE) is a superoxide indicator, and MitoSOX Red (MitoSOX) was introduced for selective detection of superoxide in the mitochondria of live cells. The intracellular ROS was measured using DHE (20 μM) staining for 30 min and MitoSOX Red (5 μM) for 60 min in PBS. Fluorescent detection was performed by flow cytometry.

Figure 13A:
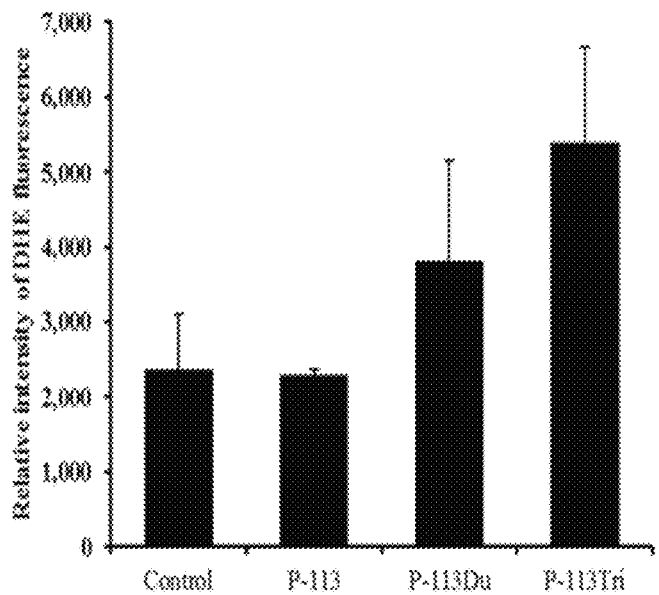
FIG. 13(A) shows the ROS assay of P-113, P-113Du and P-113Tri by using dihydroethidium (DHE) detection.
Figure 13B:
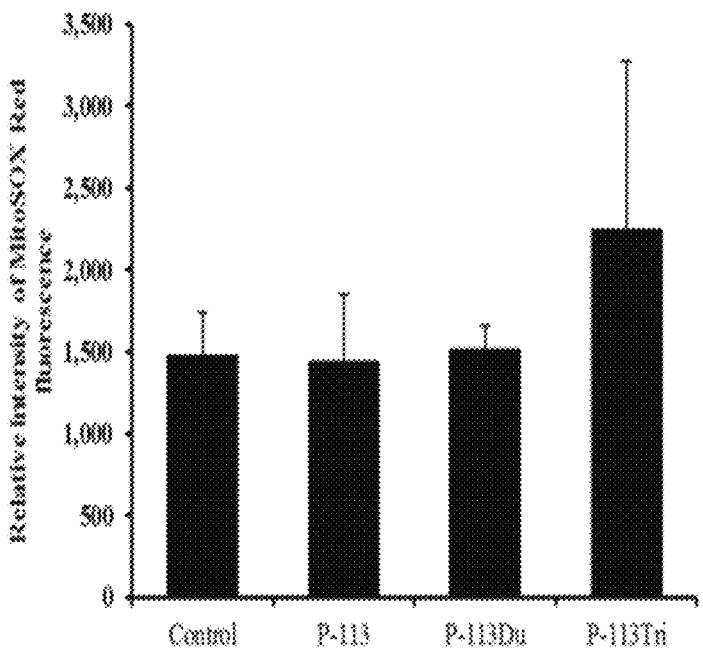
FIG. 13(B) shows the ROS assay of P-113, P-113Du and P-113Tri by using MitoSoX Red detection.

Result:

Antimicrobial peptides P-113, P-113Du and P-113Tri induced intracellular ROS formation (FIGS. 13(A) and 13(B)). P-113Tri had the strongest ROS-inducing ability, followed by P-113Du and P-113.

Example 18

The ROS scavenger diminished the candidacidal activity of P-113, P-113Du and P-113Tri for planktonic cells Method:

The SC5314 strain of *Candida albicans* (wild type or WT) were grown overnight in YPD broth at 30° C. The overnight culture was then subcultured into fresh YPD medium and grown for 5 h. Cells were harvested by centrifugation, washed twice with 12.5 mM sodium acetate (NaOAc) and resuspended in 12.5 mM NaOAc to a concentration of $8*10^6$ cells/ml. *C. albicans* cells (50 μl) were treated with or without various concentrations of peptides in the absence or presence of 50 μl of 50 mM, 100 mM L-ascorbic acid, for 1 h at 37° C. After treatment, the samples were serially diluted by 200× in PBS and 15 μl of each was spotted onto YPD agar plates. Colony-forming units were counted after 24 h incubation at 30° C. The data were represented as the mean values±SD of three independent experiments.

Figure 14A:
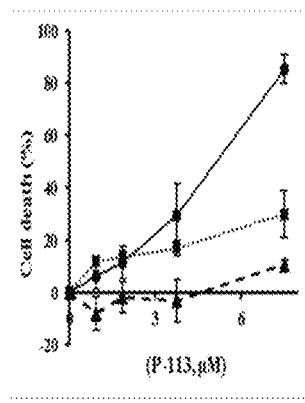
FIG. 14(A) shows the effect of ROS scavenger on P-113 activity.
Figure 14B:
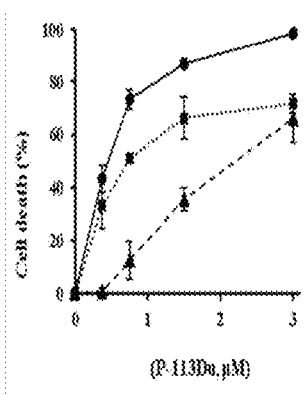
FIG. 14(B) shows the effect of ROS scavenger on P-113Du activity.
Figure 14C:
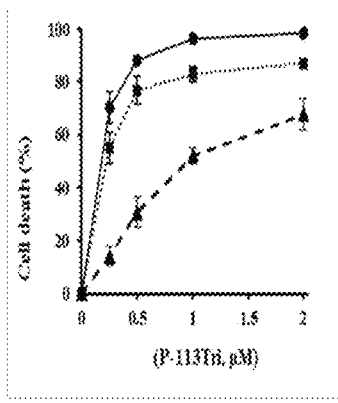
FIG. 14(C) shows the effect of ROS scavenger on P-113Tri activity.

Result:

The result indicated that the candidacidal ability of P-113, P-113Du and P-113Tri was involved in the generation of intracellular ROS (FIGS. 14(A)-14(C)). The addition of ROS scavenger (L-ascorbic acid) could diminish the candidacidal activity of the peptides tested.

Example 19

The Decrease of Oxygen Consumption in *C. albicans* Cells with the Treatment of P-113, P-113Du and P-113Tri Method:

The SC5314 strain of *Candida albicans* (wild type or WT) were grown overnight in YPD broth at 30° C. The overnight culture was then subcultured into fresh YPD medium and grown for 5 h. Cells were harvested by centrifugation, washed twice with 12.5 mM sodium acetate (NaOAc) and resuspended in 12.5 mM NaOAc to 2*10⁶ cells/ml. Cell suspensions (2 ml) were loaded into chambers of an Oroboros high resolution respirometer (Oxygraph-2k). The oxygen consumption rate was adjusted to 50 pmol/(s*ml) by increasing or decreasing the concentrations of cell suspensions. When stability of the oxygen consumption rate was reached, P-113 (1 μM), P-113Du (0.1 μM) or P-113Tri (0.05 μM) was added and the oxygen consumption rate is measured.

Figure 15A:
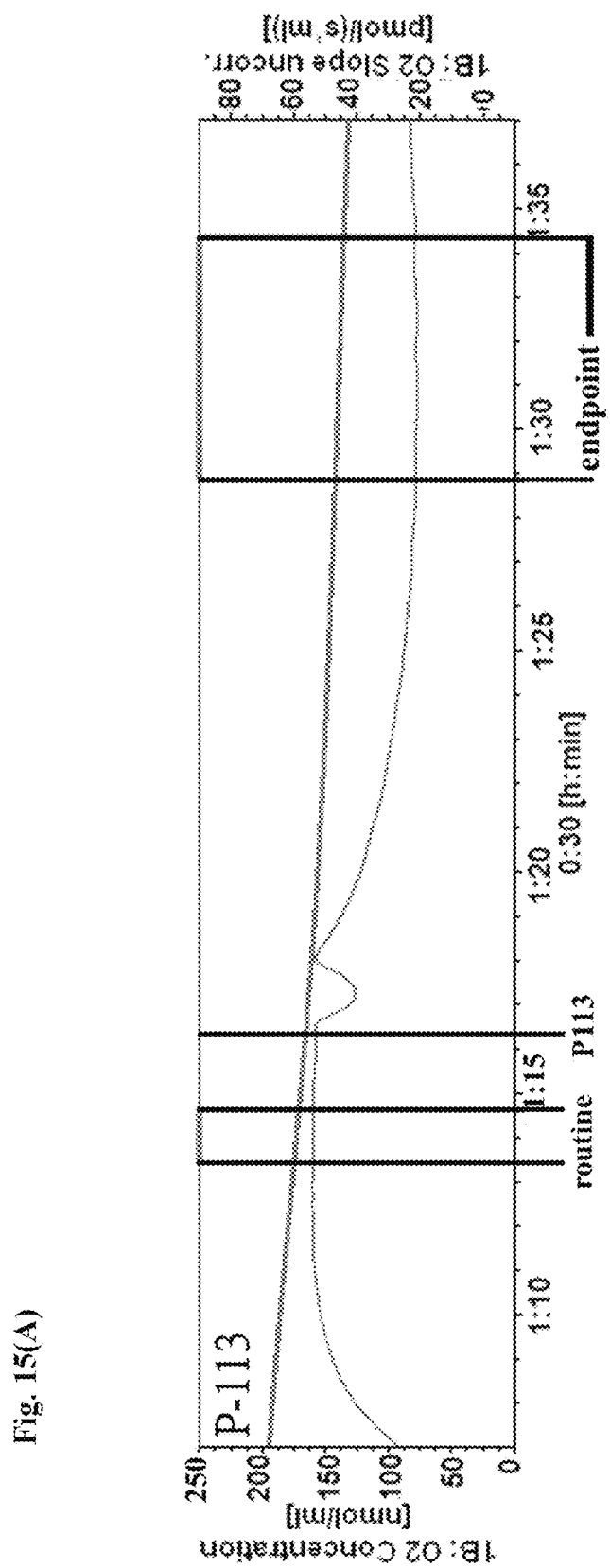
FIG. 15(A) shows the results of oxygen consumption of P-113 activity.
Figure 15B:
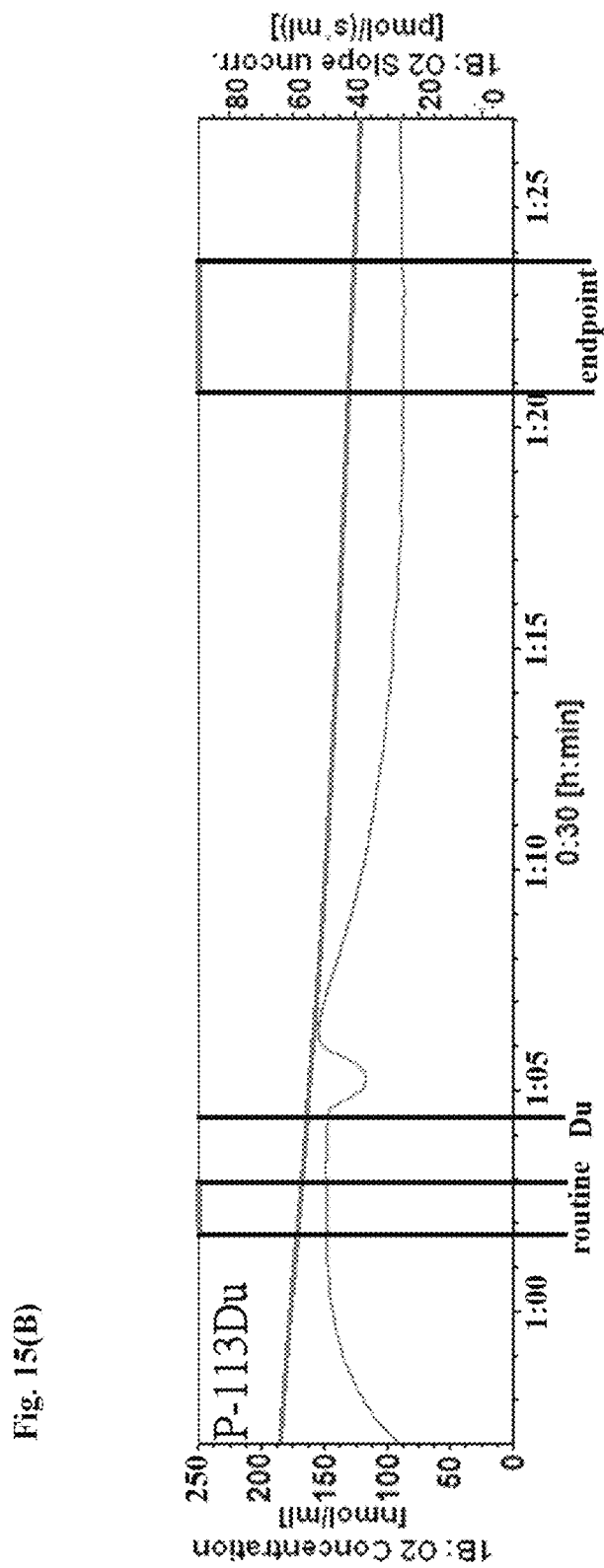
FIG. 15(B) shows the results of oxygen consumption of P-113Du activity.
Figure 15C:
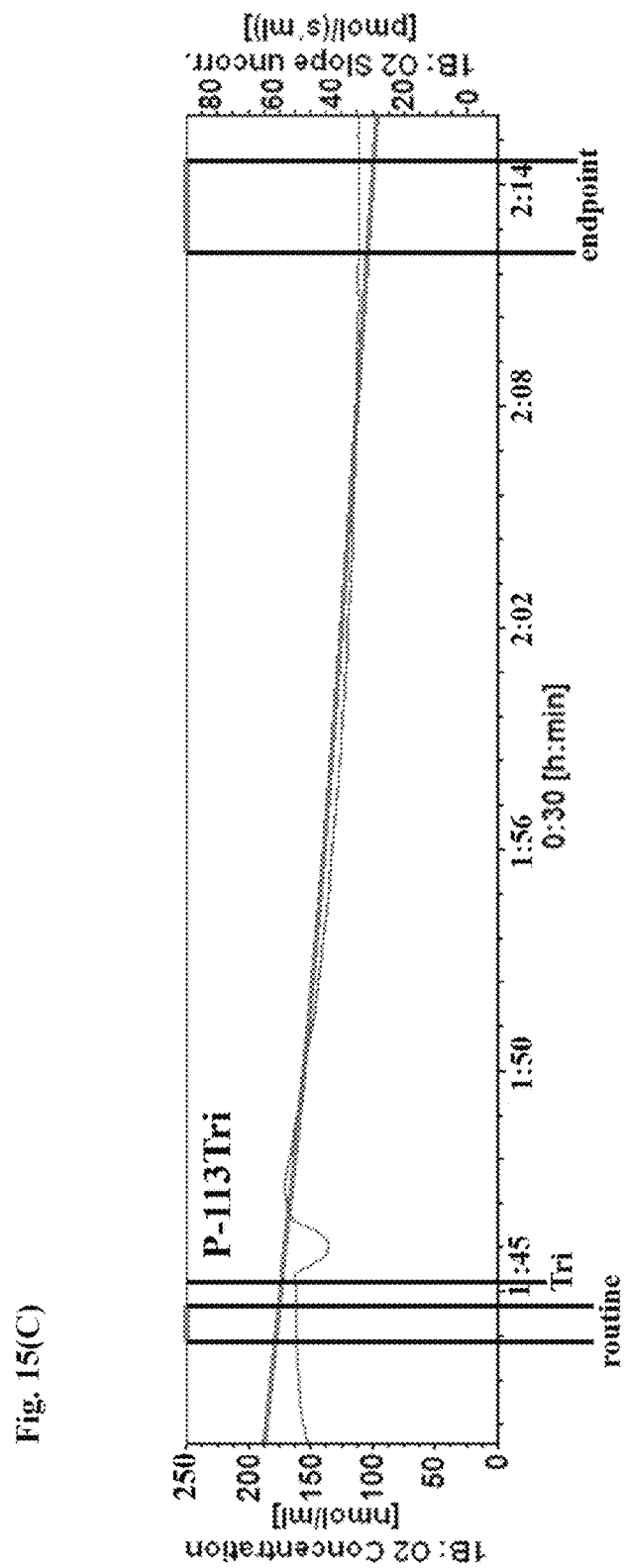
FIG. 15(C) shows the results of oxygen consumption of on P-113Tri activity.

Result:

All three peptides exhibited an inhibitory effect on the oxygen consumption rate (FIGS. 15(A)-15(C)). These results demonstrated that P-113, P-113Du and P-113Tri affected mitochondrial respiratory chain.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for treating a microbial infection in a subject, comprising administering to the subject a pharmaceutical composition, wherein the pharmaceutical composition comprises a therapeutically effective amount of a peptide consisting of SEQ ID NO: 4 or 5.

2. The method of claim 1, wherein the C terminus of SEQ ID NO: 4 is modified with a $NH_2$.

3. The method of claim 1, wherein the C terminus of SEQ ID NO: 5 is modified with a $NH_2$.

4. The method of claim 1, wherein the microbial infection is a fungal infection or a bacterial infection.

5. The method of claim 4, wherein the fungal infection is a *Candida* infection.

6. The method of claim 5, wherein the fungal infection is a *Candida albicans* infection.

7. The method of claim 4, wherein the fungal infection is a drug-resistant fungal infection.

8. The method of claim 7, wherein the drug-resistance is resistance to fluconazole, amphoterincin or caspofungin.

9. The method of claim 4, wherein the peptide destructs fungal biofilms to treat the fungal infection.

10. The method of claim 4, wherein the peptide destructs the cell wall of a fungus to treat the fungal infection.

11. The method of claim 10, wherein the peptide interacts with polysaccharides of the cell wall to destruct the cell wall of the fungus.

12. The method of claim 4, wherein the peptide induces a generation of reactive oxygen species in a fungal cell to treat the fungal infection.

13. The method of claim 12, wherein the peptide binds to mitochondria of the fungal cell to induce the generation of reactive oxygen species.

14. The method of claim 4, wherein the bacterial infection is a *Pseudomonas aeruginosa* infection, a *Klebsiella pneumonia* infection, an *Enterobacter aerogenes* infection, or a *Staphylococcus aureus* infection.

15. The method of claim 1, wherein the pharmaceutical composition comprises a pharmaceutically acceptable carrier.

16. The method of claim 1, wherein the therapeutically effective amount ranges from 1 µg to 20 µg.

* * * * *

```
                        SEQUENCE LISTING

<160> NUMBER OF SEQ ID NOS: 5

<210> SEQ ID NO 1
        <211> LENGTH: 12
        <212> TYPE: PRT
        <213> ORGANISM: Homo sapiens

<400> SEQUENCE: 1

Ala Lys Arg His His Gly Tyr Lys Arg Lys Phe His
        1               5                   10

<210> SEQ ID NO 2
        <211> LENGTH: 12
        <212> TYPE: PRT
        <213> ORGANISM: Artificial Sequence
        <220> FEATURE:
        <223> OTHER INFORMATION: Homo sapiens

<400> SEQUENCE: 2

Ala Lys Arg His His Gly His Lys Arg Lys His His
        1               5                   10

<210> SEQ ID NO 3
        <211> LENGTH: 12
        <212> TYPE: PRT
        <213> ORGANISM: Artificial Sequence
        <220> FEATURE:
        <223> OTHER INFORMATION: Homo sapiens

<400> SEQUENCE: 3

Ala Leu Leu His His Gly Tyr Lys Leu Lys Phe His
        1               5                   10

<210> SEQ ID NO 4
        <211> LENGTH: 24
        <212> TYPE: PRT
        <213> ORGANISM: Artificial Sequence
        <220> FEATURE:
        <223> OTHER INFORMATION: Homo sapiens

<400> SEQUENCE: 4

Ala Lys Arg His His Gly Tyr Lys Arg Lys Phe His Ala Lys Arg His
        1               5                   10                  15

His Gly Tyr Lys Arg Lys Phe His
                    20

<210> SEQ ID NO 5
        <211> LENGTH: 36
```

```
<212> TYPE: PRT
<213> ORGANISM: Artificial Sequence
<220> FEATURE:
<223> OTHER INFORMATION: Homo sapiens

<400> SEQUENCE: 5

Ala Lys Arg His His Gly Tyr Lys Arg Lys Phe His Ala Lys Arg His
1               5                   10                  15

His Gly Tyr Lys Arg Lys Phe His Ala Lys Arg His His Gly Tyr Lys
            20                  25                  30

Arg Lys Phe His
        35
```